(12) United States Patent
Sakamoto et al.

(10) Patent No.: US 10,106,769 B2
(45) Date of Patent: Oct. 23, 2018

(54) AUTOMATIC CULTURING DEVICE

(71) Applicant: SHIBUYA CORPORATION, Kanazawa-shi, Ishikawa (JP)

(72) Inventors: Masahiro Sakamoto, Kanazawa (JP); Noriaki Nishimura, Kanazawa (JP)

(73) Assignee: SHIBUYA CORPORATION, Kanazawa-shi, Ishikawa (JP)

( * ) Notice: Subject to any disclaimer, the term of this patent is extended or adjusted under 35 U.S.C. 154(b) by 0 days.

(21) Appl. No.: 15/322,643

(22) PCT Filed: Jun. 12, 2015

(86) PCT No.: PCT/JP2015/067024
§ 371 (c)(1),
(2) Date: Dec. 28, 2016

(87) PCT Pub. No.: WO2016/002478
PCT Pub. Date: Jan. 7, 2016

(65) Prior Publication Data
US 2017/0130189 A1 May 11, 2017

(30) Foreign Application Priority Data

Jun. 30, 2014 (JP) ................................. 2014-135300

(51) Int. Cl.
*C12M 1/36* (2006.01)
*G01N 35/02* (2006.01)
(Continued)

(52) U.S. Cl.
CPC ............ *C12M 41/48* (2013.01); *C12M 23/08* (2013.01); *C12M 23/50* (2013.01); *C12M 33/10* (2013.01); *C12M 37/00* (2013.01); *C12M 41/14* (2013.01)

(58) Field of Classification Search
CPC ....................................................... C12M 41/48
(Continued)

(56) References Cited

U.S. PATENT DOCUMENTS 9,279,143 B2    3/2016  Umeno et al.
2004/0047765 A1*  3/2004  Gordon ................... B01L 3/022
                                                                 422/63
(Continued)

FOREIGN PATENT DOCUMENTS

JP    2008-054690 A    3/2008
JP      4550101 B2     3/2008
(Continued)

OTHER PUBLICATIONS

International Search Report issued in Application No. PCT/JP2015/067024 with English translation dated Jul. 28, 2015 (5 pages).
(Continued)

*Primary Examiner* — Kevin Joyner
*Assistant Examiner* — Holly M Mull
(74) *Attorney, Agent, or Firm* — Flynn Thiel, P.C.

(57) ABSTRACT

An automatic culturing device configured such that, in a work chamber 2a maintained in a sterile state, first and second robots 6 and 7 are arranged so that the movable ranges thereof partially overlap each other, and such that liquid supply means 10 which supplies liquids, containing a culture medium and liquid medicine, to containers held by the robots, and temporary placement sections (handing-over table 42, centrifuge tube holder 43, and heated room 44), each of which hands over the containers between the first and second robots, are provided in the movable ranges of the first and second robots, which ranges overlap each other. The first robot takes out the containers housed in housing means (rotary stocker 8), and the second robot holds and
(Continued)

transports the containers handed over from the first robot via the temporary placement section.

The cultivating operation can be efficiently performed.

5 Claims, 20 Drawing Sheets

(51) Int. Cl.
| | |
|---|---|
| *G01N 35/10* | (2006.01) |
| *C12M 1/02* | (2006.01) |
| *C12M 1/24* | (2006.01) |
| *C12M 1/26* | (2006.01) |
| *C12M 1/12* | (2006.01) |
| *C12M 1/00* | (2006.01) |

(58) Field of Classification Search
USPC ........................................... 435/304.1
See application file for complete search history.

(56) References Cited

U.S. PATENT DOCUMENTS

| | | | | |
|---|---|---|---|---|
| 2012/0252110 | A1* | 10/2012 | Oura | ................... C12M 33/06 |
| | | | | 435/287.3 |
| 2012/0283867 | A1* | 11/2012 | Gelbman | ............... G01N 35/04 |
| | | | | 700/215 |
| 2014/0106386 | A1 | 4/2014 | Umeno et al. | |
| 2016/0145671 | A1 | 5/2016 | Umeno et al. | |

FOREIGN PATENT DOCUMENTS

| | | |
|---|---|---|
| JP | 2009-291104 A | 12/2009 |
| JP | 2010-158185 A | 7/2010 |
| JP | 2011-167405 A | 9/2011 |
| JP | 2012-044964 A | 3/2012 |
| JP | 2013-009618 A | 1/2013 |

OTHER PUBLICATIONS

Written Opinion of International Searching Authority issued in Application No. PCT/JP2015/067024 dated Jul. 28, 2015 (4 pages).

\* cited by examiner (a)

(b)

(a)

(b)

(a)

(b)

AUTOMATIC CULTURING DEVICE

TECHNICAL FIELD

The present invention relates to an automatic culturing device, and more particularly to an automatic culturing device which is provided with a robot in a work chamber maintained in a sterile state and performs culturing operations by the robot.

BACKGROUND ART

Today, it has been performed that, for example, cells taken from a patient are cultured for use in medical treatment, and it has been required to efficiently culture a culture object, such as the cells for use in medical treatment.

Therefore, there are known automatic culturing devices, in each of which a robot is provided inside a work chamber maintained in a sterile state, and the robot performs cultivating operations associated with the cultivation of the culture object (Patent Documents 1 and 2).

Here, the automatic culturing device described in Patent Document 2 is configured to have a robot provided with a plurality of arms, and is configured such that each of the plurality of arms holds a container, such as a dish, for housing the culture object, and operates instruments, such as a micropipette for dispensing liquids such as culture mediums.

PRIOR ART DOCUMENTS

Patent Documents

Patent Document 1 Japanese Patent No. 4550101
Patent Document 2 Japanese Patent Laid-Open No. 2013-9618

SUMMARY OF INVENTION

Problem to be Solved by the Invention

However, in the automatic culturing device of Patent Document 2 described above, there is a problem that the work is inefficient because one work is performed by using two arms, for example, such that one arm holds a micropipette, and then, the other arm operates the plunger of the micropipette.

The present invention has been made in view of the above described problem. An object of the present invention is to provide an automatic culturing device which can perform more efficiently the cultivating operation by using a plurality of robots.

Means for Solving the Problems

That is, an automatic culturing device according to the present invention is an automatic culturing device that includes, in a work chamber maintained in a sterile state, housing means which houses containers including a culture vessel and a centrifuge tube, a robot which holds and transports the containers, and liquid supply means which supplies liquids, such as a culture medium and liquid medicine, to the containers held by the robot, and is configured to perform a cultivating operation associated with the cultivation of a culture object by the robot,
the automatic culturing device being characterized by including, as the robot, first and second robots respectively having movable ranges which partially overlap with each other, and characterized in that the liquid supply means, and a temporary placement section for handing over the containers between the first and second robots are provided in the movable ranges of the first and second robots, which overlap with each other, and the first robot takes out the containers housed in the housing means, and the second robot holds the containers handed over from the first robot via the temporary placement section and transports the containers.

Advantageous Effects of Invention

According to the above-described invention, the liquid supply means is provided in the movable ranges of the first and second robots, which overlap with each other, and thereby, the liquids can be supplied to the containers by using either of the first and second robots.

Further, since the temporary placement section is provided between the first and second robots, it is possible that the first robot takes out the containers from the housing means and moves the containers to the temporary placement section, and then, the second robot receives the containers from the first robot via the temporary placement section to perform a necessary cultivating operation. Therefore, since the kinds of work are shared by the first and second robots, the cultivating operation can be efficiently performed.

MODE FOR CARRYING OUT THE INVENTION

Figure 1:
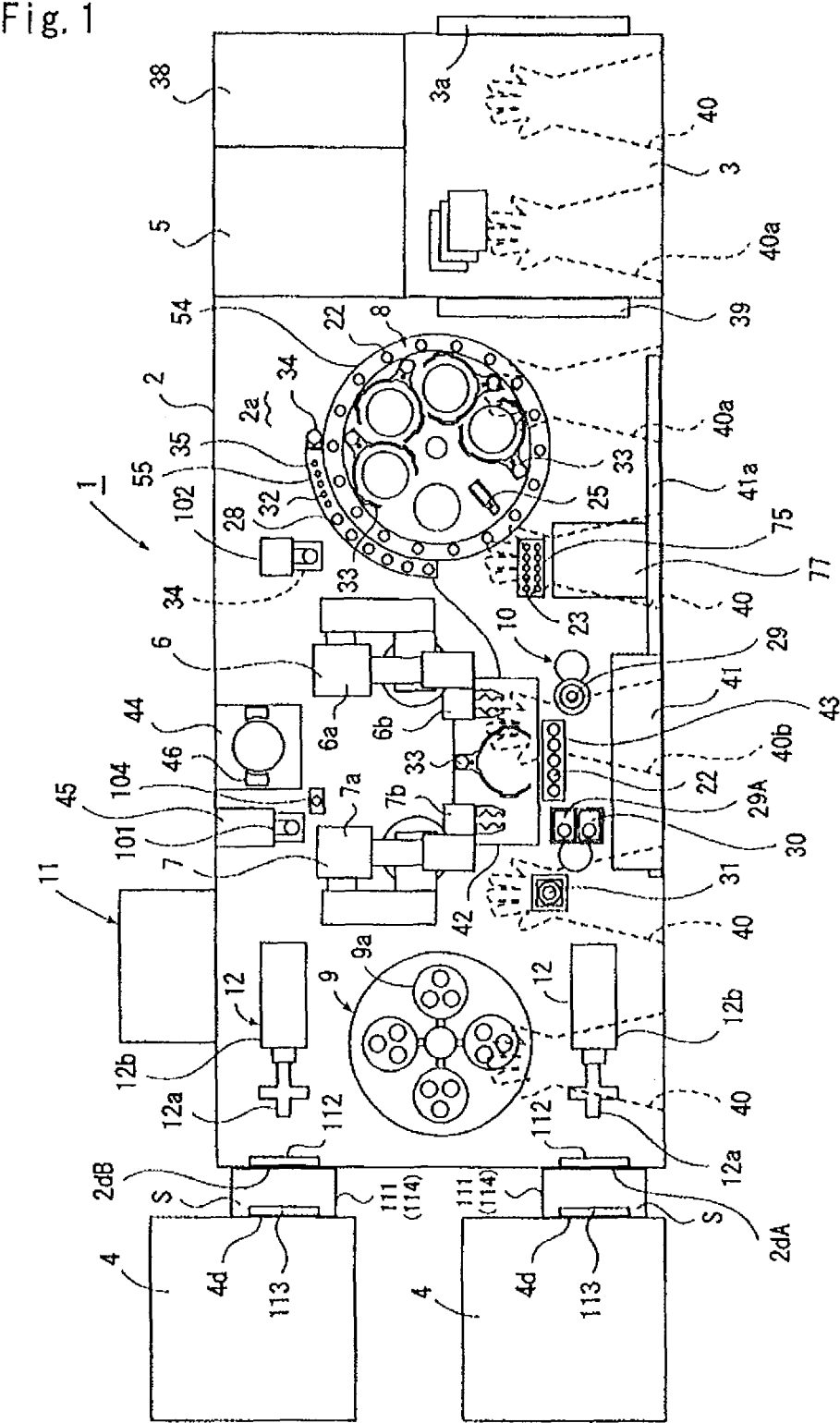
FIG. 1 is a plan view of an automatic culturing device according to a present embodiment.
Figure 2:
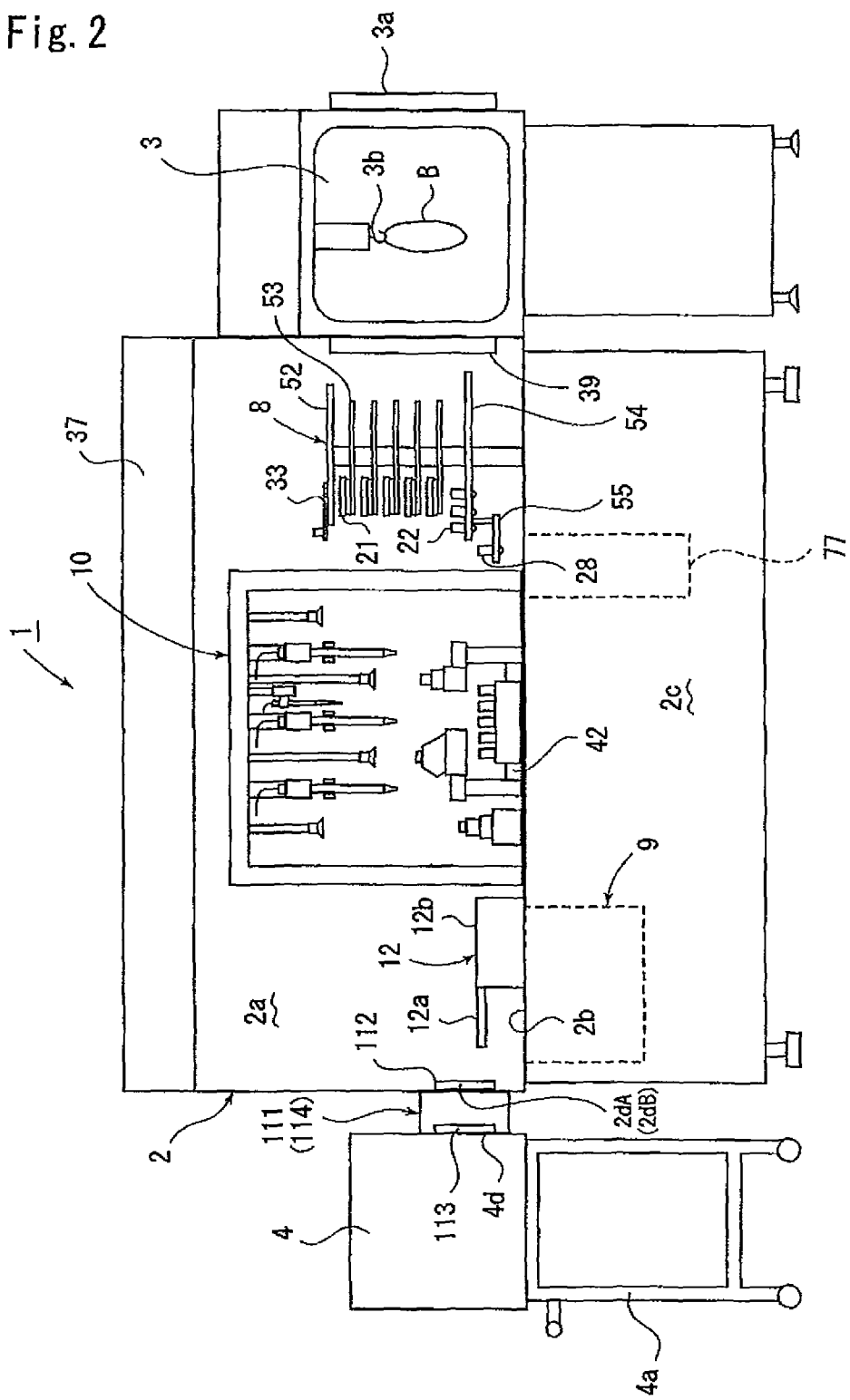
FIG. 2 is a side view of the automatic culturing device.

An illustrated embodiment will be described below. FIG. 1 is a plan view of an automatic culturing device 1 according to the present embodiment, and FIG. 2 is a side view of the automatic culturing device 1. The automatic culturing device 1 includes: an isolator 2 in which a work chamber 2a is formed and maintained in a sterile state; a pass box 3 which is connected to the work chamber 2a, and via which instruments, containers and liquids, used for cultivating operations, are carried into the work chamber 2a; and incubators 4 which are connected to the work chamber 2a and culture a culture object. The automatic culturing device 1 is controlled by control means 5 which is provided adjacent to the isolator 2.

In the work chamber 2a of the isolator 2, there are provided: a first robot 6 and a second robot 7 which hold and transport the containers; a temporary placement section which is used for handing over the containers between the first robot 6 and the second robot 7; a rotary stocker 8 as a housing means which houses the containers; a centrifugal separation means 9 which performs centrifugation; a liquid supply means 10 which supplies the liquids; an inspection means 11 which inspects the culture object, and a carrying-in-and-out means 12 which carries the culture object into and out of the incubator 4.

Further, in the present embodiment, cultivating operations, such as sowing work of sowing cells as culture objects in a culture medium, and culture medium exchange work, can be automatically performed by the first and second robots 6 and 7, and the like, under control of the control means 5.

Figure 6:
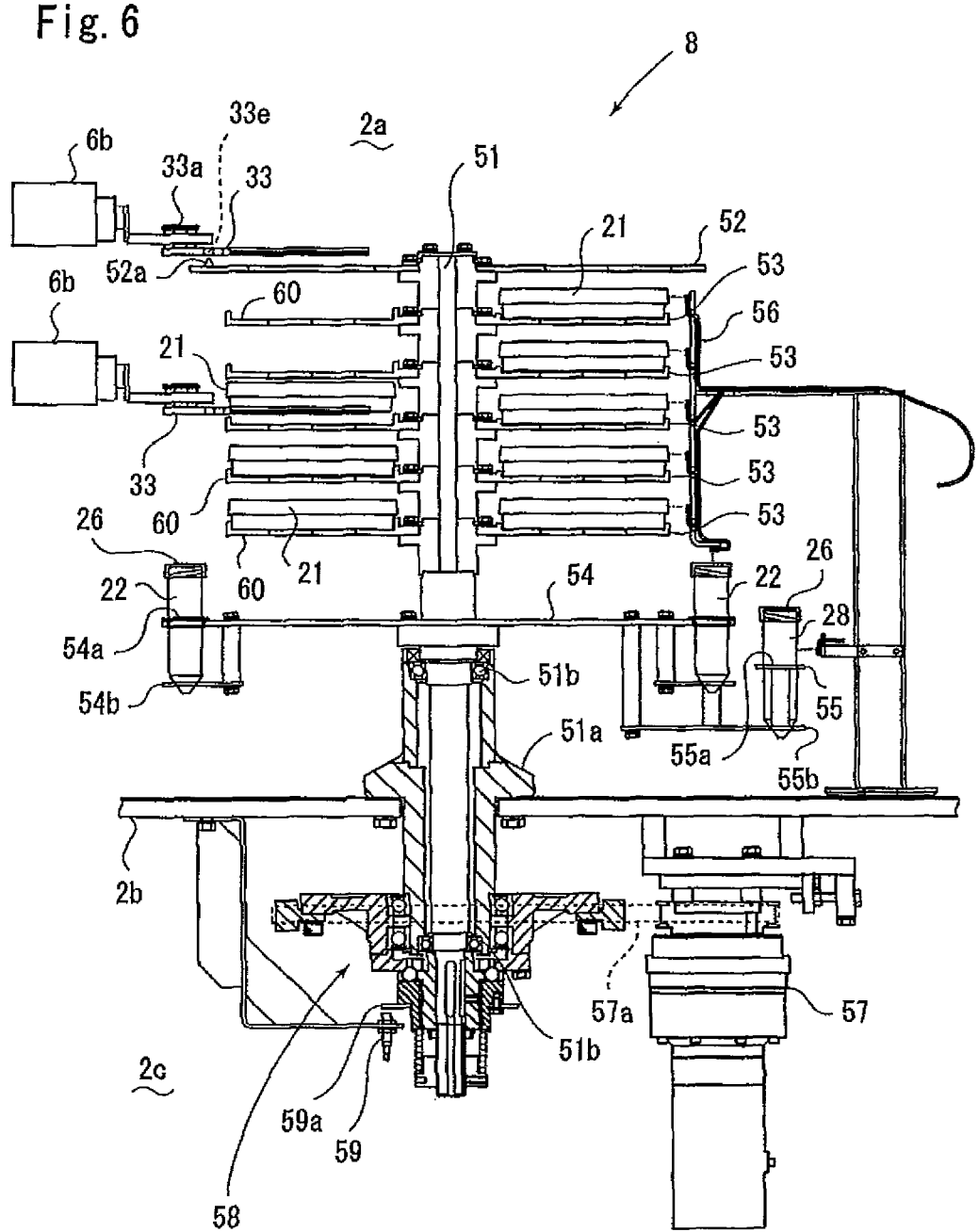
FIG. 6 is a sectional view of a rotary stocker.

As the containers used for the cultivating operations, there are a dish 21 as a culture vessel used for the culture of cells, and a centrifuge tube 22 having a tapered tip (see FIG. 6).

Further, as the instruments, there are a pipette 23 (see FIG. 9) used by the liquid supply means 10, an aspirator nozzle 24 (see FIG. 10), an observation plate 25 (see FIG. 12) used for the inspection of the cells, and a cover cap 26 (see FIG. 6 and FIG. 9) attached to the liquid container housing the centrifuge tube 22 and the liquids.

Figure 3:
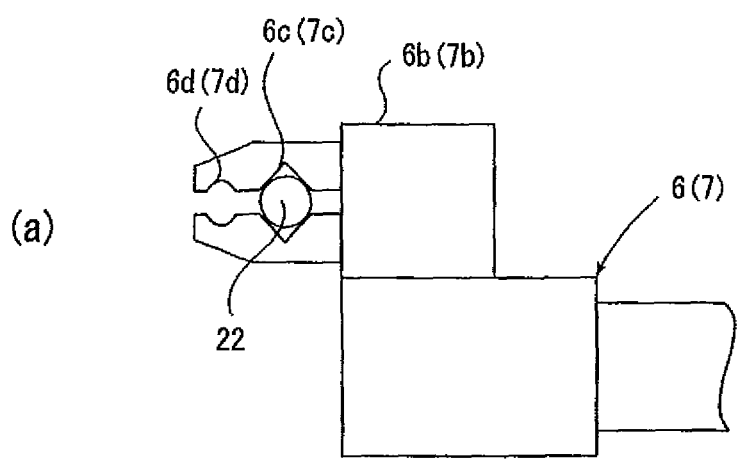
FIG. 3 is a view for explaining a gripper.
Figure 3:
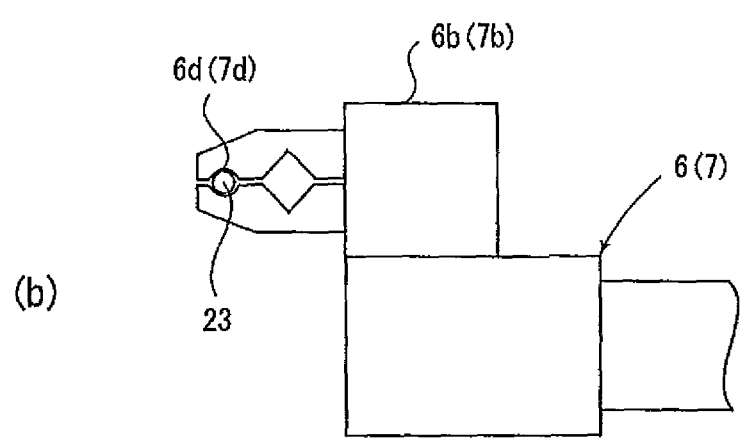

As shown in FIGS. 3(a) and 3(b), the centrifuge tube 22 and the pipette 23 are grasped by grippers 6b and 7b of the first and second robots 6 and 7. The centrifuge tube 22 is grasped by using each of V-shaped first concave sections 6c and 7c which are respectively formed in the grippers 6b and 7b and used for grasping a large diameter member. The pipette 23 is grasped by using each of arc-shaped second concave sections 6d and 7d for grasping a small diameter member.

As the culture objects, there are human tissues, blood, and the like, in addition to human cells. The culture objects are carried, as liquids, into the isolator 2 in a state of being housed in specimen containers 28 (see FIG. 6), each having the same shape as that of the centrifuge tube 22.

Further, as the liquids used for the cultivating operations, there are a culture medium, and liquid medicines, such as PBS (phosphate buffered saline), trypsin, and trypan blue. These liquids are respectively housed in a culture medium container 29, a PBS container 30, a trypsin container 31 (see FIG. 8), and a reagent container 32 (see FIG. 13).

Further, when each of the centrifuge tube 22, the specimen container 28, the culture medium container 29, the PBS container 30, and the trypsin container 31 is carried into the pass box 3, a screw cap (not shown) is screwed to the mouth section of each of the containers. However, since the opening and closing of the screw cap by the first and second robots 6 and 7 are complicated, the screw cap is exchanged for the cover cap 26 without the need for screwing in the work chamber 2a

Further, in addition, as the instruments used in the cultivating operations, there are an attachment 33 (see FIG. 4) for carrying the dish 21, and a micropipette 34 (see FIG. 13) for dispensing the reagent of the reagent container 32.

Figure 4:
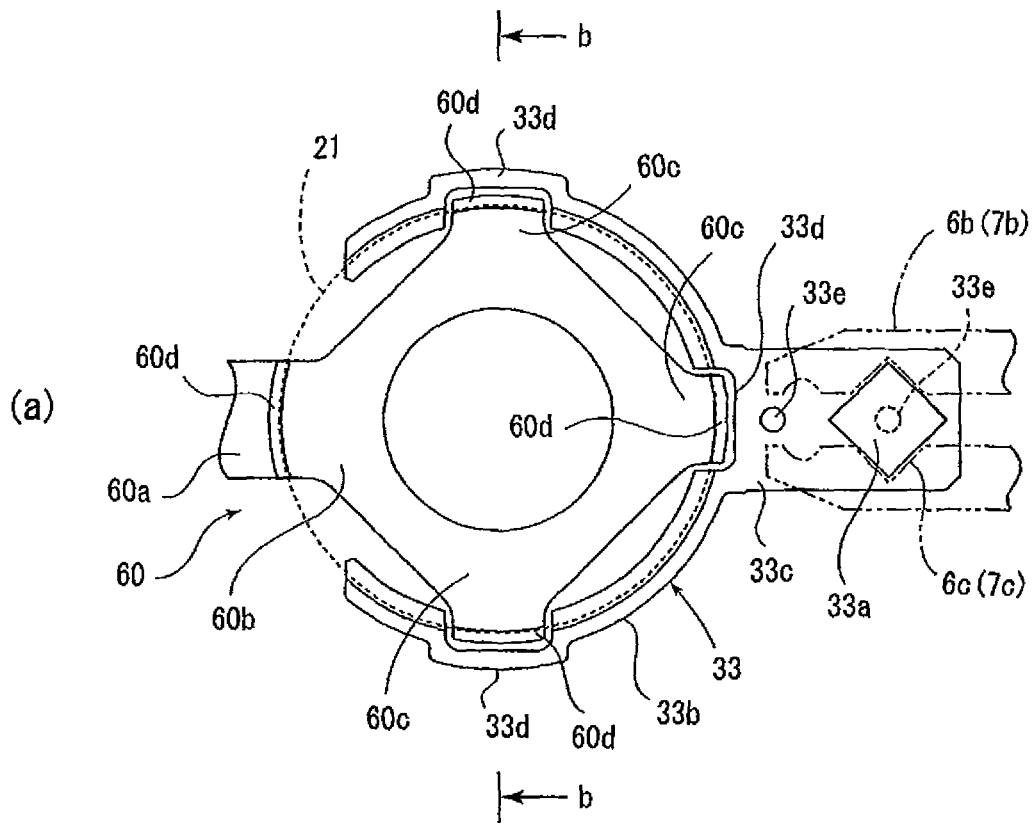
FIG. 4 is a view for explaining a mounting section of an attachment and a dish.
Figure 4:
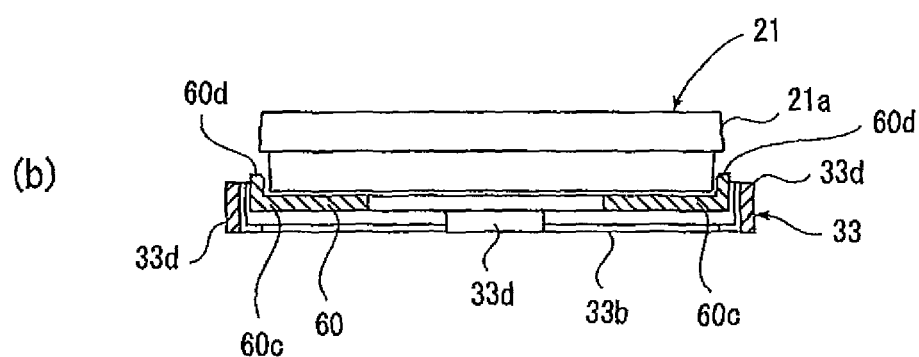

The dish 21 and the attachment 33 are described with reference to FIG. 4. The dish 21 is a circular dish-shaped container having a shallow bottom, and a cover 21a is attached to the dish 21. In FIG. 4, FIG. 4(a) is a plan view, and FIG. 4(b) is a sectional view along a line b-b in FIG. 4(a).

The attachment 33 is configured by a grip 33a grasped by the grippers 6b and 7b of the first and second robots 6 and 7, a holding section 33b which supports the dish 21, and a connecting member 33c which connects the grip 33a and the holding section 33b.

The grip 33a is a columnar member having a substantially rectangular cross section and is grasped by the V-shaped first concave sections 6c and 7c of the grippers 6b and 7b so that the attachment 33 is not rotated with respect to the grippers 6b and 7b.

The holding section 33b is a substantially U-shaped member in which the connecting member 33c is connected to the side of the U-shaped base section, and in which a necessary gap is formed at the distal end side of the holding section 33b. Further, the holding section 33b has a substantially L-shaped cross-sectional shape along the circumferential direction thereof, and is configured such that the bottom surface of the dish 21 is supported upward by the bottom surface portion of the holding section 33b, and such that the side surface of the dish 21 is supported by the side surface portion of the holding section 33b.

Further, escape sections 33d protruding to the outside of the holding section 33b are respectively formed at the base side portion of the U-shape holding section 33b and at the positions of the holding section 33b which are located at a right angle to the base side portion. The escape section 33d is configured by vertical wall surfaces.

Further, two positioning holes 33e are bored in the connecting member 33c. One of the positioning holes 33e is provided between the holding section 33b and the grip 33a, and the other of the positioning holes 33e is provided at the position of the grip 33a.

It should be noted that, in the cultivating operations, when, other than the dish 21 shown in FIG. 4, a small diameter dish smaller than the dish 21 is used, it is possible that a disk-shaped holder, having substantially the same diameter as the outer diameter of the dish 21, is provided on the lower surface of the small diameter dish, and that the small diameter dish is held by the attachment 33 together with the holder.

Figure 12:
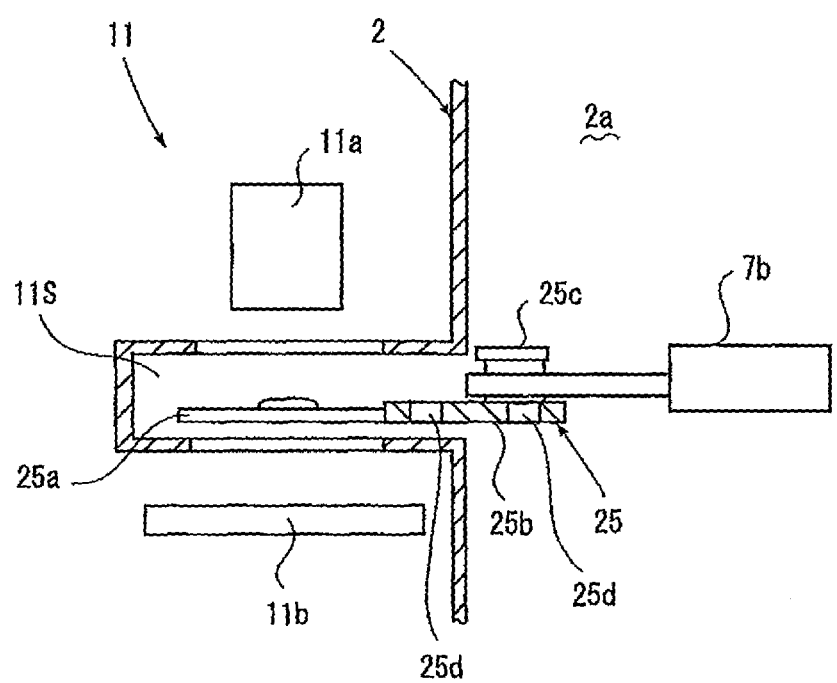
FIG. 12 is a sectional view showing an inspection means.

As shown in FIG. 12, the observation plate 25 is configured by a plate 25a which is made of glass, or the like, and on the surface of which cells are mounted, and by a plate holder 25b which holds the plate 25a.

The plate holder 25b is a substantially U-shaped thin plate member formed to surround substantially three sides of the plate 25a, and is provided with two positioning holes 25d, and a grip 25c grasped by the grippers 6b and 7b of the first and second robots 6 and 7.

Figure 13:
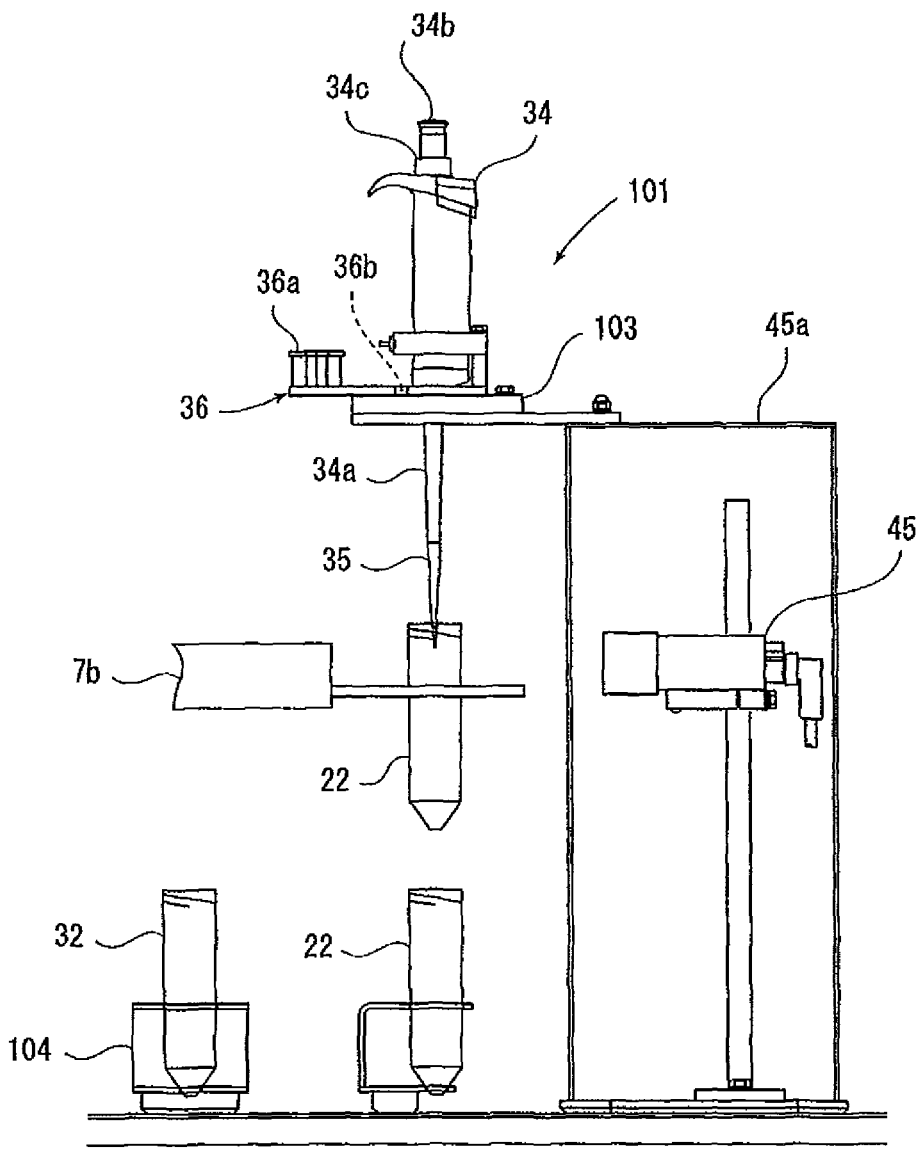
FIG. 13 is a side view showing a reagent supply means.
Figure 14:
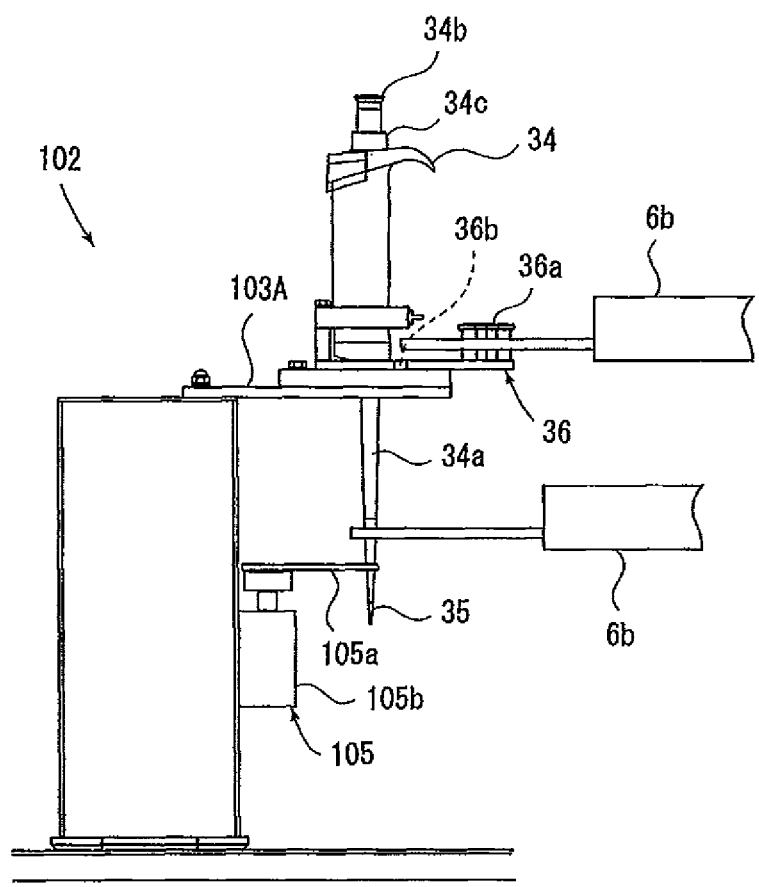
FIG. 14 is a side view showing a nozzle exchange means.

As shown in FIG. 13 and FIGS. 14, a conventionally known micropipette 34 can be used as the micropipette 34. The micropipette 34 is configured by a cylindrical distal end tube 34a to which an exchangeable micropipette nozzle 35 is mounted, and a suction button 34b for performing suction and discharge of a liquid, and an eject button 34c provided to surround the suction button 34b and to detach the micropipette nozzle 35.

Further, in order that the micropipette 34 is held by the first and second robots 6 and 7, a plate-like holding member 36 is fixed to the body portion of the micropipette 34.

The holding member 36 is provided with two positioning holes 36b, and a grip 36a having a portion which protrudes sideward of the micropipette 34 and which is grasped by the grippers 6b and 7b of the first and second robots 6 and 7.

The isolator 2 is configured such that, in a state where the work chamber 2a formed in the isolator 2 is decontaminated in advance, a sterile state maintaining means 37, provided on the upper portion of the isolator 2 shown in FIG. 2, makes cleaned air to flow from top to bottom so that the inside of the isolator 2 is maintained at a positive pressure and thereby maintained in a sterile state.

Further, in the work chamber 2a, when different cells are handled, or when different cultivating operations are performed, the inside of the work chamber 2a is decontaminated by decontamination gas supply means 38 (see FIG. 1) which supplies decontamination gas (hydrogen peroxide vapor).

The pass box 3 is provided at the outer right side of the isolator 2, and the interior space of the pass box 3 is decontaminated by the decontamination gas supplied from the decontamination gas supply means 38.

Further, the work chamber 2a of the isolator 2 and the interior space of the pass box 3 can be made to communicate with each other by opening and closing an opening and closing door 39, which is opened when the articles, such as instruments, containers, and liquids, in the pass box 3, are carried into the work chamber 2a of the isolator 2.

Further, the pass box 3 is provided with an external opening and closing door 3a for the outer space, and the articles are carried into the pass box 3 via the external opening and closing door 3a.

The instruments and the containers, which are carried into the work chamber 2a via the pass box 3, are radiation-sterilized beforehand in a state of being housed in a resin packaging bag B shown in FIG. 2. When the packaging bag B is carried into the work chamber 2a, the outer surface of the packaging bag B is decontaminated by the decontamination gas of the decontamination gas supply means 38.

A hook 3b for hanging the packaging bag B is provided in the pass box 3, and thereby, the entire outer surface of the packaging bag B can be decontaminated by attaching the decontamination gas to the entire outer surface of the packaging bag B.

On the other hand, when the specimen containers 28 and liquids are carried into the work chamber 2a via the pass box 3, the decontamination by decontamination gas is not performed for the specimen container 28 and the liquid containers 29 to 32 housing the liquids, in order to avoid the decontamination gas from entering the inside of the containers. In this case, the specimen container 28 and the liquid containers 29 to 32 are carried into the pass box 3 after the packaging bag is carried into the work chamber 2a.

At this time, the surfaces of the specimen container 28 and the liquid containers 29 to 31 are sterilized by being wiped off by using antiseptic solutions, such as alcohol (ethanol for disinfection), oxydol (aqueous hydrogen peroxide solution), peracetic acid, and sodium hypochlorite, which are carried into the pass box 3.

Further, the work of carrying the articles, such as the instruments, the containers and the liquids, into the work chamber 2a from the pass box 3, and the work of arranging the articles in the work chamber 2a are performed manually by a worker wearing gloves 40 respectively provided at the front wall portions of the isolator 2 and the pass box 3.

The glove of the globes 40, which is provided adjacent to the opening and closing door 39, is a carrying-in-and-out glove 40a for performing the carrying in and out of the articles between the pass box 3 and the work chambers 2a.

When the articles are carried from the pass box 3 into the work chamber 2a by using the carrying-in-and-out glove 40a, the worker first wears the carrying-in-and-out glove 40a provided adjacent to the opening and closing door 39 and on the side of the isolator 2. Then, the worker manually opens the opening and closing door 39.

In this state, when the worker moves the article in the pass box 3 to the inside of the work chamber 2a by using the carrying-in-and-out glove 40a on the side of the pass box 3, the worker can receive the article by using the carrying-in-and-out glove 40a on the side of the isolator 2.

It should be noted that one worker can wear the carrying-in-and-out gloves 40a to perform the above work, but each of two workers can wear each of the carrying-in-and-out gloves 40a to perform the above work.

However, among the articles carried into the work chamber 2a via the pass box 3, the aspirator nozzle 24 and the liquid containers 29 to 32, which are used by the liquid supply means 10, cannot be arranged at predetermined positions, because the work range of the carrying-in-and-out glove 40a is limited.

Therefore, in the present embodiment, arrangement gloves 40b, for arranging the aspirator nozzle 24 and the liquid containers 29 to 32 in the liquid supply means 10, are provided approximately in the center of the work chamber 2a, and further, a moving table 41, which is moved between the work range of the carrying-in-and-out glove 40a and the work range of the arrangement glove 40b, is provided.

Along a rail 41a provided in the left-right direction on the front side of the work chamber 2a, the moving table 41 is moved by the manual work of the worker wearing the carrying-in-and-out gloves 40a.

The moving table 41 is configured to receive thereon the aspirator nozzle 24 as an instrument used by the liquid supply means 10, and is configured to receive thereon, as liquid containers, the culture medium container 29, the PBS container 30, and the trypsin container 31.

The aspirator nozzles 24 and the liquid containers 29 to 31 are carried from the pass box 3 to the work chamber 2a, and then, are mounted to the moving table 41 by the worker wearing the carrying-in-and-out gloves 40a.

Then, the worker moves the moving table 41 into the work range of the arrangement glove 40b, and further, the worker wearing the arrangement glove 40b arranges the aspirator nozzles 24 and the liquid containers 29 to 31 at the predetermined positions of the liquid supply means 10, respectively.

As the first and second robots 6 and 7, it is possible to use the same type industrial articulated robots. The first and second robots 6 and 7 are arranged in the central portion of the work chamber 2a so that the movable ranges of the first and second robots 6 and 7 partially overlap each other. The first robot 6 is provided on the side of the pass box 3, and the second robot 7 is provided on the side of the incubator 4.

Each of the first and second robots 6 and 7 is provided with each of arms 6a and 7a each having a plurality of axis, and is provided with each of the grippers 6b and 7b, each of which is provided at the distal ends of each of the arms 6a and 7a. Further, the first and second robots 6 and 7 are protected against the decontamination gas.

Further, the present embodiment is provided with: a handing-over table 42 which is a temporary placement section for handing over the containers between the first robot 6 and the second robot 7 and on which the dish 21 and the observation plate 25 are mounted; a centrifuge tube holder 43 which supports the centrifuge tube 22; and a heated room 44 to which the dish 21 housing the cells is handed over.

Further, on the back side of the isolator 2, a camera 45 is provided, which images the centrifuge tube 22, the containers such as the pipette 23, the instruments, and the like, which are held by the first and second robots 6 and 7.

The handing-over table 42 is provided substantially in the middle between the first robot 6 and the second robot 7, and also, positioning pins (not shown), which are fitted into the positioning holes 25d and 33e respectively formed in the observation plate 25 and the attachment 33, are provided on the upper surface of the handing-over table 42.

For example, when the dish 21 is handed over from the first robot 6 to the second robot 7, the dish 21 having the attachment 33 mounted thereon is mounted on the handing-over table 42 by the first robot 6.

In this case, the positioning hole 33e of the attachment 33 is fitted to the positioning pin of the handing-over table 42, and thereby, the attachment 33 is mounted at a predetermined position without a positional shift.

Then, the second robot 7 holds the grip 33a of the attachment 33 mounted on the handing-over table 42, so that the handing over of the dish 21 is completed.

Further, similarly to the handing over of the attachment 33, the handing over of the observation plate 25 can be performed between the first robot 6 and the second robot 7. Further, the handing-over table 42 may also be used when only the dish 21 is handed over between the first robot 6 and the second robot 7.

The centrifuge tube holder 43 is provided at a position adjacent to the front of the handing-over table 42, and is configured to support a plurality of the centrifuge tubes 22.

Similarly to the handing over of the case of the dish 21, the handing over of the centrifuge tubes 22 can be performed on the centrifuge tube holder 43 by the first and second robots 6 and 7. Further, since a plurality of the centrifuge tubes 22 can be supported by the centrifuge tube holder 43, it is possible that while one of the robots performs the required work, the other of the robots repeatedly performs other work and then puts the plurality of centrifuge tubes 22 on the centrifuge tube holder 43 for supporting them.

Figure 5:
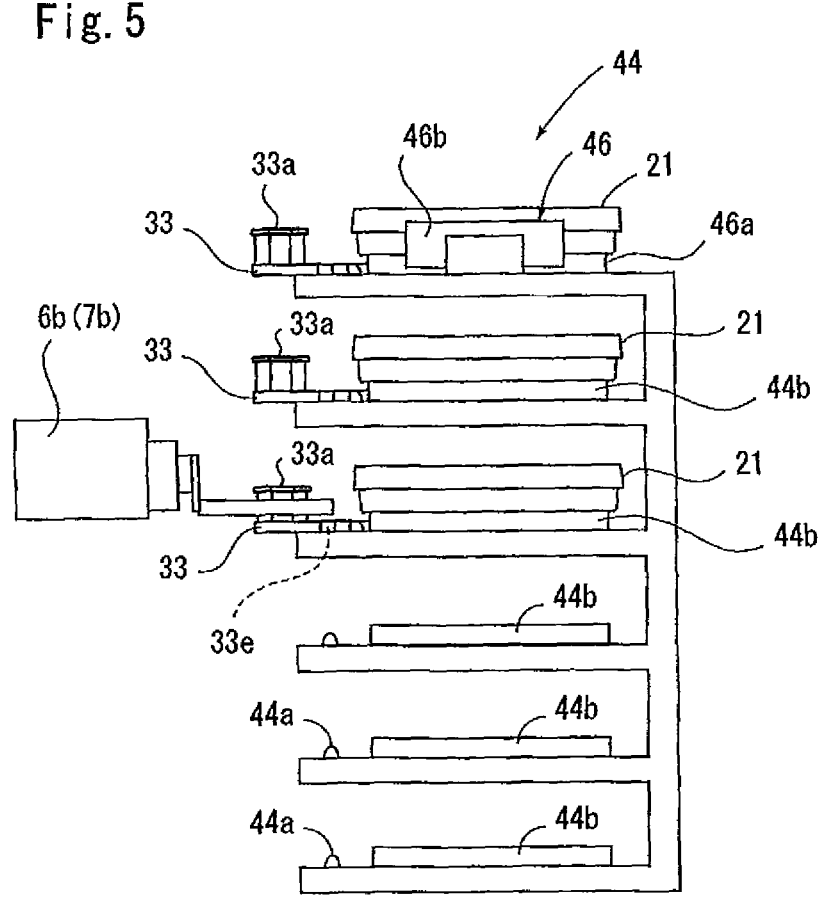
FIG. 5 is a sectional view of a heated room.

As shown in FIG. 5, the heated room 44 is configured to house the five dishes 21 each having the attachment 33 attached thereto and, in the case of the cultivating operation, tapping means 46 for giving a vibration to the dish 21 is provided in the uppermost stage.

Further, each of the stages of the heated room 44 is provided with a positioning pin 44a for positioning the attachment 33, and a plate-like heating means 44b. The heating means 44b is configured, when the dish 21 is mounted, to be brought into close contact with the bottom surface of the dish 21 and heat the dish 21 to a predetermined temperature.

The tapping means 46 is configured by a plate-like mounting section 46a to which the dish 21 is mounted, and a hitting member 46b which is provided to sandwich the mounting section 46a and which is reciprocated by drive means, such as an air cylinder.

The hitting member 46b is reciprocated to collide with the side surface of the dish 21 and thereby, during culturing, cells sticking to the bottom surface of the dish 21 are vibrated to be peeled off from the bottom surface of the dish 21.

Further, similarly to the handing-over table 42, the handing over of only the attachment 33 can also be performed between the first and second robots 6 and 7 by using the heated room 44.

The camera 45 is provided so that its imaging range is set in the vicinity of the handing-over table 42. In practice, as shown in FIG. 13, the camera 45 is provided in a casing 45a for protecting the camera 45 against a decontamination gas.

The centrifuge tube 22 and the pipette 23, which are held by the first and second robots 6 and 7, are moved in the imaging range of the camera 45. The camera 45 images the centrifuge tube 22 and the pipette 23, and the control means 5 confirms whether or not the grippers 6b and 7b normally hold the centrifuge tube 22 and the pipette 23.

Further, the camera 45 can image the inside of the centrifuge tube 22 held by the grippers 6b and 7b, to confirm the remaining amount of the liquid, and the like, in the centrifuge tube 22.

As shown in FIG. 6, the rotary stocker 8 is configured by a rotating shaft 51 rotatably provided on a floor 2b of the work chamber 2a, and by a sheet of attachment mounting table 52, five sheets of dish mounting table 53, a sheet of centrifuge tube supporting table 54, and a sheet of specimen container supporting table 55, which tables are provided from the upper side of the rotating shaft 51 in that order.

Further, at a position adjacent to the rotary stocker 8, a container detection sensor 56 for recognizing the presence or absence of containers mounted on the tables 53 to 55 is provided.

The rotating shaft 51 is rotatably erected, via a bearing 51b, on a tubular member 51a fixed by penetrating the floor 2b of the work chamber 2a formed in the isolator 2 and also, a drive means 57 made of a servo motor is connected to a portion of the rotating shaft 51, which portion protrudes from the floor 2b into a space 2c.

Further, between the rotating shaft 51 and the drive means 57, switching means 58 is provided, which switches between the transmission state of transmitting the driving force of the drive means 57 to the rotating shaft 51, and the non-transmission state of interrupting the driving force of the drive means 57 to allow the rotating shaft 51 to be manually rotated. In the non-transmission state, each of the tables 52 to 55 can be manually rotated.

Further, a rotation position sensor 59 is provided at a position adjacent to the lower end portion of the rotating shaft 51, and a detection piece 59a detected by the rotation position sensor 59 is provided at the lower end portion of the rotating shaft 51.

Further, when the rotation position sensor 59 detects the detection piece 59a, the control means 5 recognizes the rotation angle of the rotating shaft 51, and controls the drive means 57 so that each of the containers, respectively mounted on the tables 52 to 55, is moved to and stopped at a required handing-over position.

The five attachments 33 and the one observation plate 25 can be mounted to the attachment mounting table 52, and positioning pins 52a, fitted to the positioning holes 33e and 25d respectively provided in the attachments 33 and the observation plate 25, are provided.

The four dishes 21 can be mounted to each of the five dish mounting tables 53 and, in particular, dish mounting sections 60 shown in FIG. 4 are provided in four directions about the rotating shaft 51.

The dish mounting section 60 is configured by a connection section 60a connected to the rotating shaft 51, a mounting section 60b formed at the distal end of the connection section 60a, a protruding piece 60c radially protruding from the peripheral edge of the mounting section 60b, and engaging protrusions 60d each protruding upward from the distal end of each of the protruding pieces 60c.

The protruding piece 60c is provided at the position corresponding to the gap on the distal end side and the escape section 33d of the attachment 33. Further, the engaging protrusion 60d is provided to correspond to the outer diameter position of the dish 21, and supports the side surface of the dish 21.

The attachment 33 and the dish mounting section 60 are arranged so that the handing over of the dish 21 is performed in the direction shown in FIG. 4(a), and the control means 5 controls the first robot 6 and the drive means 57 of the rotary stocker 8 to realize the arrangement of the figure.

Specifically, the control means 5 performs the control such that the gap of the distal end side of the holding section 33b of the attachment 33 held by the first robot 6 does not interfere with the connection section 60a of the dish mounting section 60, and such that the escape section 33d of the attachment 33 does not interfere with the protruding piece 60c of the mounting section 60b.

Then, the control means 5 performs the control such that, in the state where the dish 21 is mounted to the mounting section 60b, the first robot 6 moves the attachment 33 to the upper portion from the lower portion of the mounting section 60b, so that the dish 21 is handed over to the first robot 6 from the rotary stocker 8.

On the other hand, in the state where the dish 21 is mounted to the attachment 33 held by the first robot 6, the first robot 6 moves the attachment 33 from the upper portion to the lower portion of the mounting section 60b, so that the dish 21 is handed over to the rotary stocker 8 from the first robot 6.

The centrifuge tube supporting table 54, which protrudes outward in the radial direction to have a larger diameter than the outer peripheral edge of the dish mounting table 53, is provided with a plurality of hole portions 54a which are formed along the outer peripheral edge of the centrifuge tube supporting table 54 and each of which supports the outer peripheral surfaces of the centrifuge tube 22. Further, the centrifuge tube supporting table 54 is provided with a receiving member 54b which is formed under the hole portions 54a and supports the lower end portion of the centrifuge tube 22. Thereby, the centrifuge tubes 22 are supported at equal intervals in the upright state.

In this way, the supporting section of the centrifuge tube 22 is arranged outward from the dish mounting table 53 and thereby, the first robot 6 can upwardly extract the centrifuge tube 22 held by the centrifuge tube supporting table 54.

The specimen container supporting table 55 is an arc-shaped member having a larger diameter than the centrifuge tube supporting table 54. Similarly to the centrifuge tube supporting table 54, the specimen container supporting table 55 is provided with hole portions 55a and receiving members 55b along the circumferential direction of the arc-shaped member, and is configured to support the specimen container 28 and the reagent container 32 in the upright state, and to support the micropipette nozzle 35 of the micropipette 34 in the upright state.

Further, the specimen container supporting table 55 can hold the micropipette 34, and hence, positioning pins (not shown), engaging the two positioning holes 36b formed in the holding member 36 of the micropipette 34, are provided at the end portions of the specimen container supporting table 55.

It should be noted that, although not described in each working of the following cultivating operation, the specimen container supporting table 55 is configured to be able to support the centrifuge tube 22 housing a required reagent, and the like, used in the cultivating operation.

Further, each of the tables 52 to 55 is configured to be positioned at least partially in the movable range of the first robot 6, and is configured such that the required containers, and the like, mounted to the tables 52 to 55, are positioned at predetermined handing-over positions in the movable range of the first robot 6 by control of the control means 5.

Thereby, the first robot 6 can hold all of the containers, the instruments, and the like, housed in the rotary stocker 8. Thereby, a number of the containers, the instruments, and the like, can be housed in the work chamber 2a of the isolator 2, and efficiently taken out from the work chamber 2a of the isolator 2, as a result of which the cultivating operation can be efficiently performed.

Further, the tables 52 to 55 are arranged in multiple stages in the vertical direction along the rotating shaft 51, and hence, the ratio of the tables 52 to 55 occupying the floor 2b of the work chamber 2a can be reduced, so that the containers and the instruments can be compactly housed.

Further, the portion of each of the tables 52 to 55, which portion is adjacent to the carrying-in-and-out glove 40a provided on the front of the isolator 2, is located in the work range of the carrying-in-and-out glove 40a.

As a result, the worker wearing the carrying-in-and-out glove 40a is able to carry the containers, and the like, from the pass box 3 into the work chamber 2a, and then, to bring the switching means 58 into the non-transmission state. Thereby, the worker can manually rotate each of the tables 52 to 55 so that the containers, and the like, are housed in the rotary stocker 8.

Figure 7:
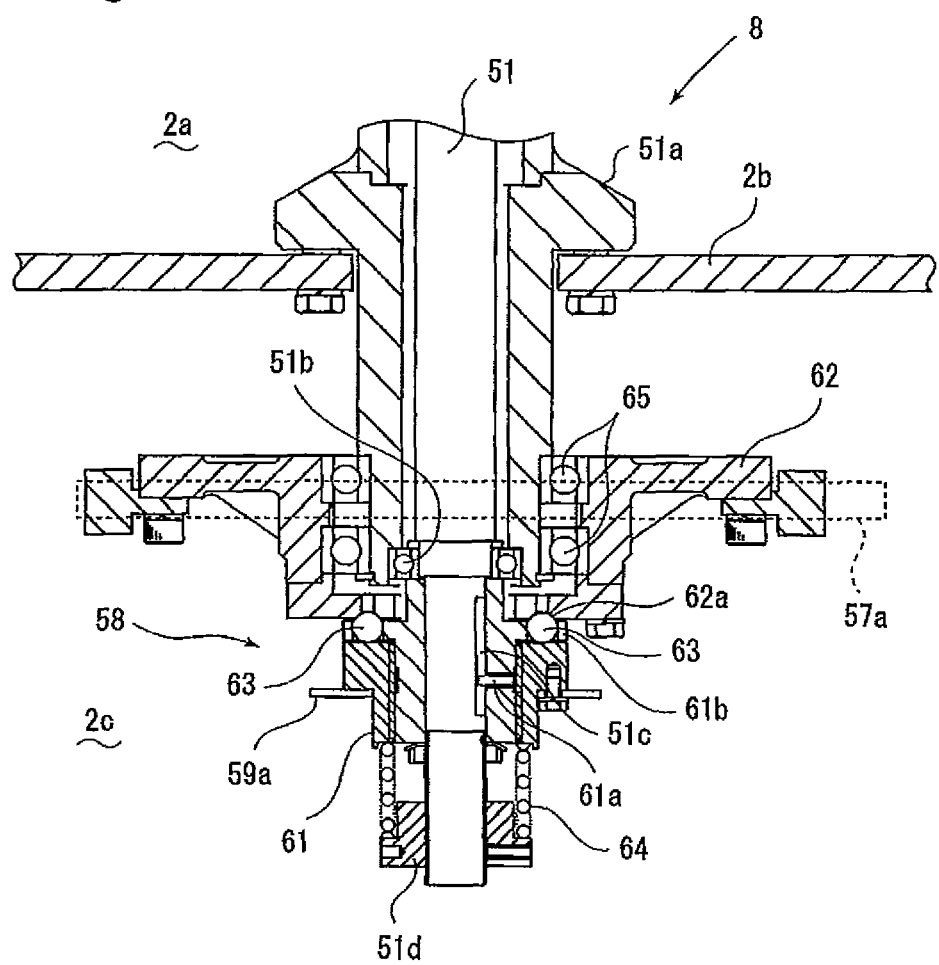
FIG. 7 is a sectional view of a switching means.

FIG. 7 shows a sectional view of the switching means 58 of the rotary stocker 8. The switching means 58 includes a connecting member 61 rotated integrally with the rotating shaft 51, a pulley 62 rotatably provided on the tubular member 51a, and a plurality of balls 63 provided between the connecting member 61 and the pulley 62.

A key 61a is provided on the inner surface of the connecting member 61, and a key groove 51c is provided in the vertical direction on the outer surface of the rotating shaft 51. When the key 61a and the key groove 51c engage with each other, the connecting member 61 and the rotating shaft 51 are rotated integrally, and the connecting member 61 is movable in the vertical direction with respect to the rotating shaft 51.

Further, a spring 64 is elastically mounted between the lower end portion of the connecting member 61 and a spring receiver 51d provided at the lower end portion of the rotating shaft 51, and thereby, the connecting member 61 is constantly urged in the upward direction.

The pulley 62 is located on the upper portion of the connecting member 61, and is rotatably held at the lower end portion of the tubular member 51a via ball bearings 65.

Further, a belt 57a is stretched between the pulley 62 and the drive means 57, so that the driving force of the drive means 57 acts on the pulley 62.

The balls 63 are housed, in a falling-off manner, in a plurality of concave sections 61b formed on the upper surface of the connecting member 61 along the circumferential direction. Further, a substantially hemispherical concave section 62a, to which the top portion of each of the balls 63 is fitted, is formed on the lower surface of the pulley 62.

The switching means 58 shown in FIG. 7 is in the transmission state. In the transmission state, the ball 63 is fitted to the concave section 62*a* formed on the lower surface of the pulley 62.

At this time, the connecting member 61 is urged upward by the spring 64, and hence, the state where the ball 63 is fitted to the concave section 62*a* is maintained by the urging force of the spring 64.

For this reason, in the transmission state, the pulley 62 is rotated by the drive means 57 via the belt 57*a*, and thereby, the driving force is transmitted to the connecting member 61 via the ball 63, to rotate each of the rotary tables 52 to 55 fixed to the rotating shaft 51.

Further, for switching the switching means 58 from the transmission state to the non-transmission state, it is only necessary that the ball 63 be detached from the concave section 62*a* of the pulley 62 so that the pulley 62 and the connecting member 61 can be rotatable with respect to each other.

More specifically, when the switching means 58 is set in the non-transmission state, first, the drive means 57 is not operated, and the rotation of the pulley 62 is prevented via the belt 57*a*.

In this state, when the worker manually rotates the tables 52 to 55, the switching means 58 is in the transmission state at first, and hence, a resistance force from the pulley 62 preventing rotation is applied to the worker.

The worker further rotates the tables 52 to 55 against this resistance force, and thereby, the ball 63 is disengaged from the concave section 62*a* of the pulley 62, so that the connecting member 61 is lowered against the urging force of the spring 64.

When the ball 63 is disengaged from the concave section 62*a*, the ball 63 becomes movable from the lower surface of the pulley 62, and the connecting member 61 becomes rotatable with respect to the pulley 62, so that the worker can rotate the tables 52 to 55 with little force.

Further, when the worker further rotates the tables 52 to 55, the ball 63 is again fitted to the concave section 62*a* of the pulley 62, and the connecting member 61 is moved upward by the urging force of the spring 64, so that the switching means 58 is again in the transmission state.

It should be noted that the switching means 58 may not be the mechanical switching means having the above-described configuration, and may be, for example, a switching means for turning off the servo command of a servo motor as the above-described drive means 57.

As shown in FIG. 1, the centrifugal separation means 9 is provided between the second robot 7 and the incubator 4, and a conventionally known centrifugal separator can be used as the centrifugal separation means 9.

As shown in FIG. 2, the centrifugal separation means 9 is provided to protrude downward from the floor 2*b* of the work chamber 2*a* of the isolator 2, and has four buckets 9*a* provided at the rotating shaft which is rotated by a motor (not shown) substantially at the center of the centrifugal separation means 9. The centrifuge tube 22 is housed in the bucket 9*a*.

Further, in the present embodiment, at least a part of the centrifugal separation means 9 is in the movable range of the second robot 7, and the required bucket 9*a* is positioned in the movable range of the second robot 7 by control of the control means 5.

Further, at the time of centrifuging, a counterweight to be provided at a position opposing that of the centrifuge tube 22 housing the cells or the like, can be created by dispensing PBS into a new centrifuge tube 22 from the liquid supply means 10 and using operation of the first robot 6 and the second robot 7.

Figure 8:
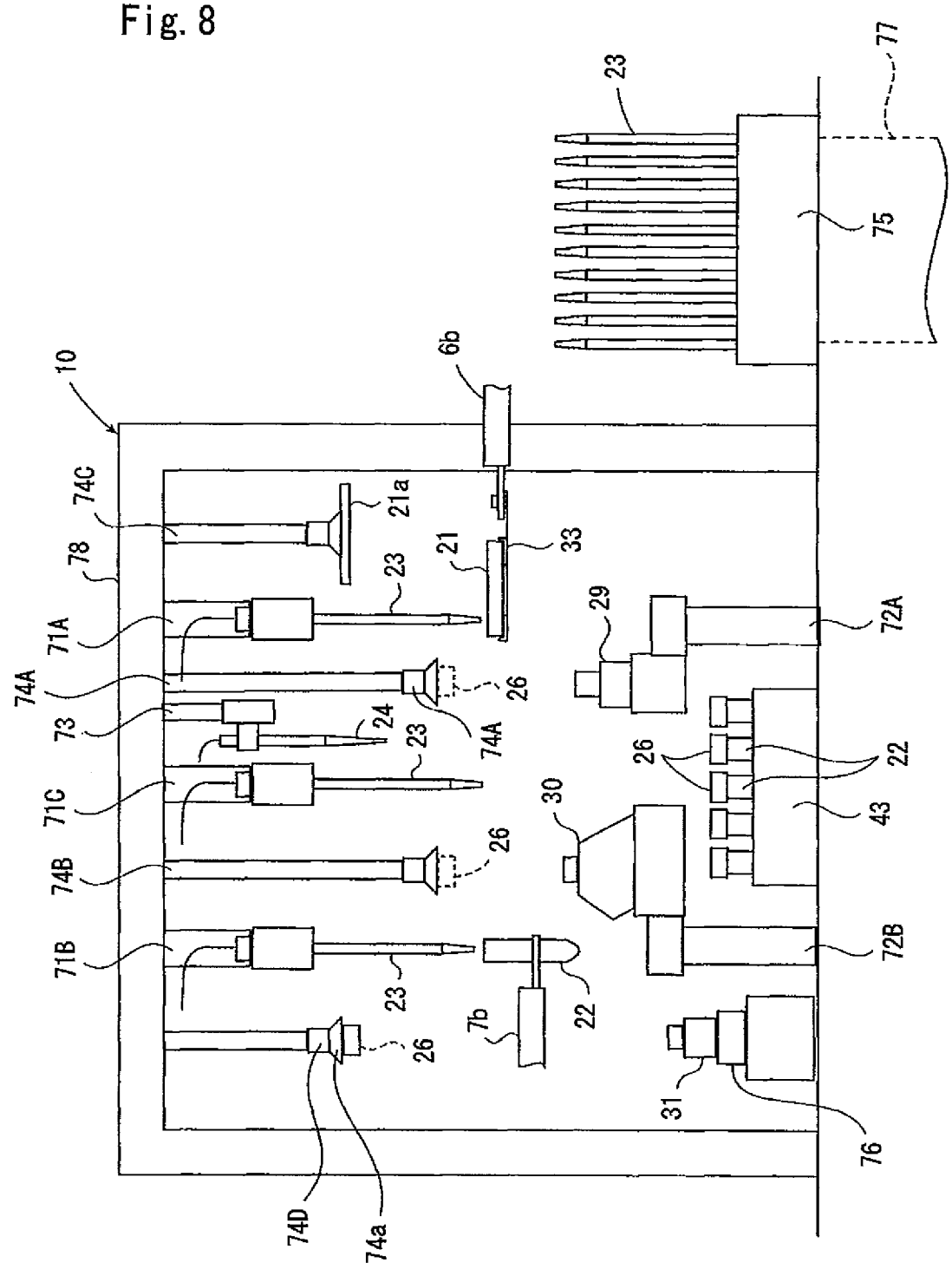
FIG. 8 is a view showing a configuration of a liquid supply/discharge means.

As shown in FIG. 8, the liquid supply means 10 is configured by first to third liquid supply/discharge means 71A to 71C for dispensing liquid, first and second container holding means 72A and 72B for holding the liquid containers 29 and 30 which house liquids, an aspirator 73 for sucking and removing unnecessary liquid, and first to fourth lid holding means 74A to 74D for holding cover caps 26 attached to the centrifuge tube 22 and the liquid containers 29 to 31, and for holding the cover 21*a* of the dish 21.

In the above-described configuration, the first liquid supply/discharge means 71A and the first container holding means 72A configure a culture medium supply means which supplies a culture medium to the containers, and the third liquid supply/discharge means 71C configures a dispensing means which dispenses a culture object to the containers.

Further, a pipette holder 75 as a pipette support section for housing a plurality of the pipettes 23, a container holder 76 for housing the trypsin container 31, and a disposal box 77 as a disposal section for discarding the used pipette 23 and the used centrifuge tube 22 are provided in the vicinity of the liquid supply means 10.

The first to third liquid supply/discharge means 71A to 71C, the aspirator 73, and the first to fourth lid holding means 74A to 74D are provided in a upper portion of the work chamber 2*a* by a substantially gate-shaped holding member 78, and each of these is located in the movable range of each of the first and second robots 6 and 7.

Further, in particular, the first liquid supply/discharge means 71A is provided on the side of the first robot 6, and the second liquid supply/discharge means 71B is formed on the side of the second robot 7, and the third liquid supply/discharge means 71C is provided between the first liquid supply/discharge means 71A and the second liquid supply/discharge means 71B.

The first container holding means 72A is provided at a lower portion of the first liquid supply/discharge means 71A, and the second container holding means 72B is provided at a lower portion of the second liquid supply/discharge means 71B.

The first and second lid holding means 74A and 74B are provided respectively at upper portions of the first and second container holding means 72A and 72B, and the third lid holding means 74C is arranged in the vicinity of the first robot 6, and the fourth lid holding means 74D is arranged in the vicinity of the second robot 7.

The container holder 76 for housing the trypsin container 31 is provided in the movable range of the second robot 7, and the trypsin container 31 is held by the second robot 7 together with the container holder 76.

In the following, the second liquid supply/discharge means 71B, the second container holding means 72B, and the second lid holding means 74B are described with reference to FIG. 9. It should be noted that the description of the first and third liquid supply/discharge means 71 A and 71 C having the same configuration as that of the liquid supply/discharge means 71B, and the description of the first container holding means 72A having substantially the same configuration as that of the second container holding means 72B are omitted.

The second liquid supply/discharge means 71B is configured by a connecting section 79 fixed to the holding member 78 and connected to the pipette 23, an elevating means 80 for holding the pipette 23 and connecting the pipette 23 to the connecting section 79, and a supply/discharge means 81 connected to the connecting section 79 and provided in the space 2c below the floor 2b of the work chamber 2a.

The connecting section 79 is a tubular member made of a resin and having a bellows shape and is fixed to the holding member 78 via a stay. A tube 7 is arranged between the upper portion of the connecting section 79 and the supply/discharge means 81, and the lower portion of the connecting section 79 is in close contact with the pipette 23.

The elevating means 80 is configured by a gripper 80a which is opened and closed by an air cylinder, or the like, to grip the pipette 23, and an air cylinder 80b for raising and lowering the gripper 80a.

Further, in the state where the pipette 23 is held by the gripper 80a, when the air cylinder 80b positions the pipette 23 at the raised position, the upper end portion of the pipette 23 is brought into close contact with the connecting section 79 while compressing the connecting section 79, so that the supply/discharge means 81 and the pipette 23 are made to communicate with each other.

The supply/discharge means 81 is provided at each of the first to third liquid supply/discharge means 71A to 71C. By control of the control means 5, the supply/discharge means 81 makes the pipette 23 suck and hold a predetermined amount of liquid, and makes the pipette 23 discharge a predetermined amount of the liquid held by the pipette 23.

The second container holding means 72B is configured by: a holding member 82 holding the PBS container 30 and a culture medium container 29A housing a non-adjusted culture medium; and a moving means 83 for raising and lowering the holding member 82.

The mouth section 30a of the PBS container 30, which is used in the present embodiment, is provided to be inclined with respect to the bottom section 30b, and the holding member 82 holds the bottom section 30b of the PBS container 30 in the inclined state.

Thereby, the corner portion formed by the bottom section 30b and the side portion adjacent to the bottom section 30b are located just under the mouth section 30a. When the pipette 23 is inserted in the mouth section 30a from just above, the distal end of the pipette 23 is positioned at the corner portion.

On the other hand, although not shown, the culture medium container 29A has a prismatic form, and a mouth portion is formed in the upper portion of the culture medium container 29A. The holding member 82 holds the culture medium container 29A in the state where the bottom portion of the culture medium container 29A is oriented horizontally.

Further, the first container holding means 72A holds the culture medium container 29 housing an adjusted culture medium, and the culture medium container 29 also has a tubular shape having a mouth portion at the upper portion thereof, and is held in the state where the bottom portion thereof is oriented horizontally.

The moving means 83 is configured by an elevating mechanism 84 for raising and lowering the holding member 82, and a rotating mechanism 85 for rotating the holding member 82 in the horizontal direction, and raises and lowers the PBS container 30 held by the holding member 82 and turns the PBS container 30 in the lateral direction.

The elevating mechanism 84 is configured by a cylindrical support column 84a vertically penetrating the work chamber 2a, an elevating member 84b fixed to the holding member 82 and provided so as to be movable vertically along the support column 84a, and a slide mechanism 84c for raising and lowering the elevating member 84b.

The elevating member 84b is provided with a coupling rod 84d extending downward, and the slide mechanism 84c raises and lowers the elevating member 84b via the coupling rod 84d.

The rotating mechanism 85 is configured by a servo motor 85a provided in the space 2c below the floor 2b of the work chamber 2a, a pulley 85b provided at the coupling rod 84d, and a belt 85c stretched between the servo motor 85a and the pulley 85b.

When the pulley 85b is driven by the servo motor 85a, the coupling rod 84d is rotated, and thereby, the elevating member 84b is rotated with respect to the support column 84a, so that the holding member 82 is rotated horizontally.

At this time, a ball link 85d is provided at the connecting portion between the lower end portion of the coupling rod 84d and the slide mechanism 84c, to allow the rotation of the coupling rod 84d.

Figure 10:
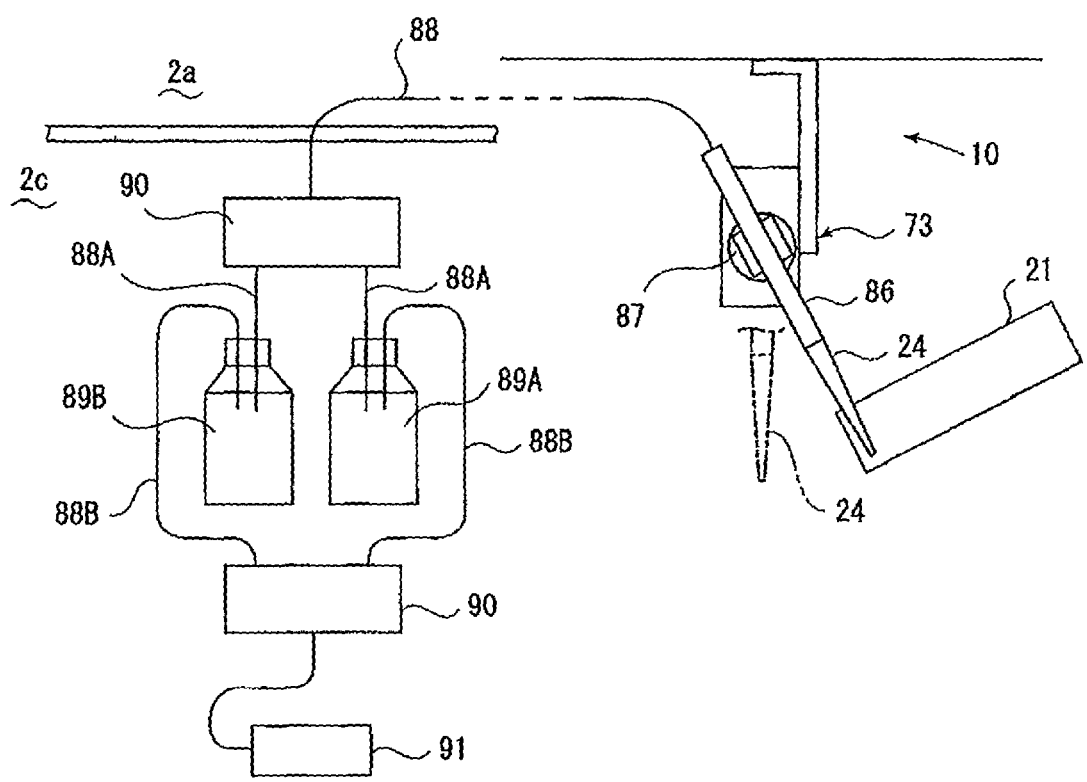
FIG. 10 is a side view of an aspirator.

FIG. 10 shows the aspirator 73 which is configured by: a suction tube 86 having the aspirator nozzle 24 attached to the distal end thereof; a rotation means 87 rotatably holding the suction tube 86; a tube 88 connected to the suction tube 86, two waste liquid bottles 89A and 89B provided in the middle of the tube 88; a switching means 90 for switching the flow path to the two waste liquid bottles 89A and 89B; and suction means 91 for generating a negative pressure in the aspirator nozzle 24.

The aspirator nozzle 24 is provided exchangeably at the distal end of the suction tube 86, and the aspirator nozzle 24 is exchanged by the worker wearing the arrangement glove 40b. It should be noted that the aspirator nozzle 24 may be exchanged by a robot.

The rotation means 87 is configured to change the inclination of the aspirator nozzle 24 attached to the suction tube 86. For example, when the liquid of the centrifuge tube 22 is discharged, the aspirator nozzle 24 is held vertically and used in the state where the centrifuge tube 22 is held vertically. When the liquid in the dish 21 is discharged, the dish 21 is inclined so that the liquid is located on the lower side thereof, and then, the aspirator nozzle 24 is inclined to correspond to the inclination of the dish 21.

The waste liquid bottles 89A and 89B are provided in the space 2c below the floor 2b of the work chamber 2a, and a tube 88A communicating with the suction tube 86, and a tube 88B communicating with the suction means 91 respectively connected to the upper portions of the waste liquid bottles 89A and 89B.

In this configuration, when the suction means 91 generates a negative pressure suction force, the negative pressure acts on the aspirator nozzle 24 via the waste liquid bottles 89A and 89B, and thereby, the liquid sucked by the aspirator nozzle 24 is collected by the waste liquid bottles 89A and 89B.

Further, while the automatic culturing device 1 is operating, the suction means 91 always generates a negative pressure, and thereby, the air in the work chamber 2a of the isolator 2 is always sucked, as a result of which the liquid in the waste liquid bottles 89A and 89B, and air in the external space are prevented from flowing into the work chamber 2a.

The tube 88 is branched to two parts respectively connected to the two waste liquid bottles 89A and 89B, and the switching means 90 is provided at the branch portion.

The switching means 90 switches the flow passage of the branched tube 88 so that one of the waste liquid bottle 89A and the waste liquid bottle 89B is made to communicate with the suction tube 86 and the suction means 91.

For example, when, during the cultivating operation, the waste liquid bottle 89A is full, the control means 5 controls the switching means 90 so that the flow passage is switched to the waste liquid bottle 89B. Thereby, while waste liquid is collected in the waste liquid bottle 89B, the fully filled waste liquid bottle 89A can be exchanged by an empty waste liquid bottle.

The first to fourth lid holding means 74A to 74D, each having a suction head 74a provided at the lower end portion thereof, suck and hold the cover 21a of the dish 21, and the cover caps 26 of the centrifuge tube 22 and the liquid containers 29 to 31.

The first and second lid holding means 74A and 74B provided above the first and second container holding means 72A and 72B temporarily hold the cover caps 26 of the culture medium container 29 and the PBS container 30 (culture medium container 29A) which are held by the first and second container holding means 72A and 72B.

The third lid holding means 74C temporarily holds the dish 21 held by the first robot 6, and the cover 21a and the cover cap 26 which are attached to the centrifuge tube 22.

Similarly, the fourth lid holding means 74D temporarily holds the dish 21 held by the second robot 7, and the cover 21a and the cover cap 26 which are attached to the centrifuge tube 22.

Figure 11:
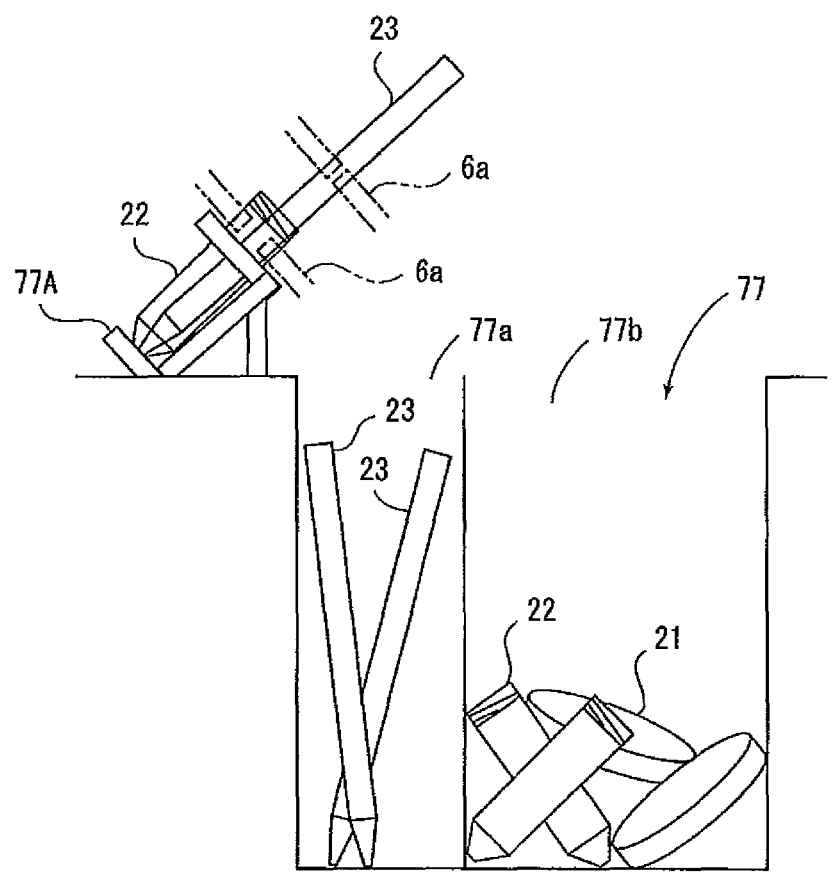
FIG. 11 is a side view of a disposal box.

As shown in FIG. 11, the pipettes 23 and the centrifuge tubes 22, which became unnecessary in the cultivating operation, are discarded in the disposal box 77, which is provided in the movable range of the first robot 6, and in the working range of the carrying-in-and-out glove 40a.

The disposal box 77 is formed to have two disposal spaces 77a and 77b arranged in front and back, and a disposal bag is set beforehand in each of the disposal spaces 77a and 77b.

In the disposal box 77, the pipette disposal space 77a on the side of the first robot 6 is a vertically long space in which the pipettes 23 are discarded, and the disposal space 77b on the wall surface side of the isolator 2 is a space for other containers, in which space the centrifuge tube 22, the dishes 21, and the like, other than the pipette 23, are discarded.

Thereby, the vertically long pipettes 23 can be aligned in the vertical direction in the pipette disposal space 77a, and thereby, the volume of wastes can be reduced compared with the case where the vertically long pipettes 23 are discarded in one space together with the centrifuge tubes 22, the dishes 21, and the like.

Further, the holding member 77A for diagonally holding the empty centrifuge tube 22 is provided at a position adjacent to the pipette disposal space 77a in the disposal box 77, and the used pipette 23 is housed in the empty centrifuge tube 22 held by the holding member 77A.

The holding member 77A holds the centrifuge tube 22 diagonally above the pipette disposal space 77a so that the upper end portion of the pipette 23 protrudes above the disposal box 77. Thereby, the pipette 23 can be positioned in the centrifuge tube 22 to be held by the robot.

The operation of the liquid supply means 10 having the above-described configuration will be described.

First, before the cultivating operation is performed in the automatic culturing device 1, the first robot 6 mounts the pipettes 23 to the first to third liquid supply/discharge means 71A to 71C.

First, by the worker wearing the carrying-in-and-out glove 40a, the pipettes 23, carried into the isolator 2 from the pass box 3, are housed in the pipette holder 75 in a state where the distal end portions of the pipettes 23 are directed upward.

Then, the first robot 6 takes out the pipette 23 from the pipette holder 75 and rotates the pipette 23 by 180° so that the distal end portion of the pipette 23 is directed downward.

In this state, the first robot 6 moves the pipette 23 to each of the first to third liquid supply/discharge means 71A to 71C.

At this time, the pipette 23 is rotated by 90° every time the pipette 23 is directly handed over between the first robot 6 and the second robot 7.

Figure 9:
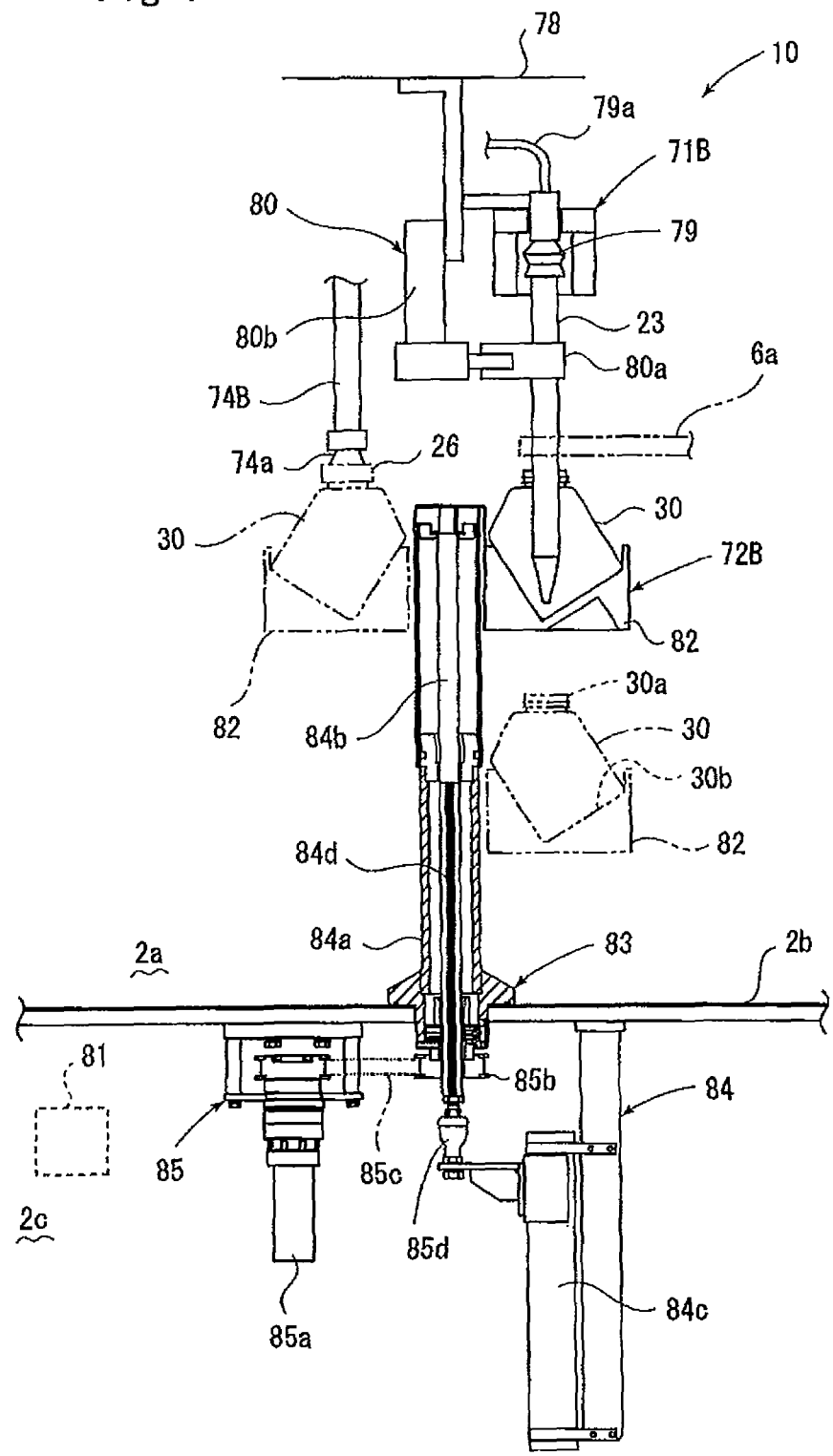
FIG. 9 is a side view of a second dispensing means and a second container holding means.

Referring to FIG. 9, in the state where the pipette 23 is mounted, the elevating means 80 positions the gripper 80a at the lowered position. In this state, the first robot 6 hands over the pipette 23 to the gripper 80a.

Then, the elevating means 80 raises the gripper 80a together with the pipette 23, to bring the upper end portion of the pipette 23 into close contact with the connecting section 79 from below. Thereby, the pipette 23 is made to communicate with the supply/discharge means 81, and the pipette 23 is held at the second liquid supply/discharge means 71B.

When an operation similar to this operation is performed, the pipettes 23 are mounted to the first and third liquid supply/discharge means 71A and 71C.

The operation when the culture medium is dispensed to the centrifuge tube 22 will be described by using the first liquid supply/discharge means 71A. It should be noted that the operation when the PBS is dispensed to the dish 21 by using the second liquid supply/discharge means 71B is the same, and hence, the description thereof is omitted.

First, when the culture medium container 29 is carried into the work chamber 2a from the pass box 3, the liquid surface height of the culture medium in the culture medium container 29 is registered beforehand in the control means 5.

Examples of the method for specifically recognizing the liquid surface height are considered to include: a method of recognizing the liquid surface height on the basis of the weight of the culture medium container 29 measured by using a weighing scale as a liquid surface height detecting means; and a method of directly measuring the liquid surface height from the mouth portion of the culture medium container 29 by using a commercially available sensor, such as an optical sensor, an ultrasonic sensor, and a capacitance sensor.

Next, a predetermined amount of the culture medium is sucked to the pipette 23 of the first liquid supply/discharge means 71A.

Specifically, the first container holding means 72A moves the culture medium container 29 to the first lid holding means 74A adjacent to the first liquid supply/discharge means 71A, so that the cover cap 26 is sucked and held.

Further, the first container holding means 72A moves the culture medium container 29 to the first liquid supply/discharge means 71A, and inserts the pipette 23 into the culture medium container 29. Then, the supply/discharge means 81 is operated so that a predetermined amount of the culture medium is sucked to the pipette 23.

At this time, the liquid surface height of the culture medium in the culture medium container 29 is registered in the control means 5, and hence, the control means 5 controls the moving means 83 of the first container holding means 72A, to adjust the relative height between the pipette 23 and the liquid surface of the culture medium of the culture medium container 29.

Specifically, the insertion amount of the pipette 23 inserted into the culture medium of the culture medium container 29 is made to correspond to a minimum depth. When the first liquid supply/discharge means 71A sucks the culture medium of culture medium container 29 and thereby the liquid surface height of the culture medium is reduced, the control means 5 controls the moving means 83 to raise the culture medium container 29 according to the reduction of the liquid surface height.

Thereby, the contact area of the culture medium adhering to the outer surface of the pipette 23 is minimized, so that the culture medium adhering to the outer surface of the pipette 23 is prevented from falling in the work chamber 2a.

Then, when the culture medium is sucked from the culture medium container 29, the first container holding means 72A moves the culture medium container 29 to the first lid holding means 74A to attach the cover cap 26 to the culture medium container 29, and then, lowers the culture medium container 29 to a lowered position.

In this way, when the predetermined amount of the culture medium is sucked to the pipette 23 of the first liquid supply/discharge means 71A, then the operation, in which the culture medium is discharged, for example, to the centrifuge tube 22 held by the second robot 7, is performed.

Specifically, the second robot 7 is operated to take out the centrifuge tube 22 from the centrifuge tube holder 43, and moves the centrifuge tube 22 to the fourth lid holding means 74D adjacent to the second robot 7, to make the fourth lid holding means 74D hold the cover cap 26.

Then, when the second robot 7 positions the centrifuge tube 22 below the pipette 23 of the first liquid supply/discharge means 71A, the control means 5 controls the supply/discharge means 81 so that a predetermined amount of the culture medium housed in the pipette 23 is discharged to the centrifuge tube 22.

At this time, the control means 5 memorizes the amount of the liquid housed in the centrifuge tube 22, and the second robot 7 adjusts the relative height between the pipette 23 and the centrifuge tube 22 held by the second robot 7.

When a liquid containing a predetermined amount of cells is housed in the centrifuge tube 22 beforehand, the second robot 7 positions the centrifuge tube 22 so that the distal end of the pipette 23 is positioned slightly above the liquid surface of the liquid.

Then, when the culture medium is discharged from the pipette 23, so that the liquid surface height is increased, the second robot 7 lowers the centrifuge tube 22 in accordance with the increase of the liquid surface height, and thereby prevents the liquid in the centrifuge tube 22 from being in contact with the pipette 23.

When the predetermined amount of the culture medium is dispensed to the centrifuge tube 22 in this way, the second robot 7 moves the centrifuge tube 22 to the fourth lid holding means 74D to mount the cover cap 26 to the centrifuge tube 22.

The first liquid supply/discharge means 71A handles the culture medium housed in the culture medium container 29 of the first container holding means 72A, and the second liquid supply/discharge means 71B handles the PBS housed in the PBS container 30 of the second container holding means 72B. On the other hand, the third liquid supply/discharge means 71C of the present embodiment handles the trypsin housed in the trypsin container 31. The trypsin is used, for example, when a suspension, composed of the culture medium and a liquid containing cells, is prepared in the centrifuge tube 22.

First, when the trypsin is dispensed, the second robot 7 holds the trypsin container 31 together with the container holder 76, to make the fourth lid holding means 74D temporarily hold the cover cap 26, and then makes the third liquid supply/discharge means 71C suck the trypsin.

At this time, the control means 5 registers the liquid surface height of the trypsin in the trypsin container 31, and increases the trypsin container 31 as the trypsin is sucked to the pipette 23, and thereby, the liquid surface height of the trypsin is reduced.

Thereafter, the third liquid supply/discharge means 71C completes the dispensation of the trypsin. Then, when preparing the suspension, the third liquid supply/discharge means 71C exchanges the pipette 23 used for dispensing the trypsin for a new pipette 23.

The first robot 6 takes out the empty centrifuge tube 22 supported by the holding member 77 provided in the vicinity of the disposal box 77 beforehand, and positions the empty centrifuge tube 22 below the pipette 23 of the third liquid supply/discharge means 71C.

Then, the elevating means 80 of the third liquid supply/discharge means 71C lowers the pipette 23 so that the pipette 23 is detached from the connecting section 79. Further, the elevating means 80 releases the holding pipette 23, so that the pipette 23 drops into the centrifuge tube 22 held by the first robot 6.

The first robot 6 operates such that the centrifuge tube 22 housing the pipette 23 is housed in the holding member 77A, and thereby, the centrifuge tube 22 and the pipette 23 are in an inclined state.

As a result, the pipette 23 is surely located under the opening portion of the inclined centrifuge tube 22, and hence, the first robot 6 can surely grasp the pipette 23.

When taking out the pipette 23 from the inclined centrifuge tube 22, the first robot 6 rotates the pipette 23 in the vertical direction. Further, the first robot 6 positions the pipette 23 above the pipette disposal space 77a in the disposal box 77 and drops the pipette 23.

The pipette 23 drops vertically, and hence, even when another pipette 23 is thereafter discarded, all the pipettes 23 in the pipette disposal space 77a are oriented in the vertical direction, so that the volume at the time of disposal can be reduced.

In this way, the pipette 23 is allowed to drop into the centrifuge tube 22 held by the first robot 6, and hence, it is possible that the pipette 23 housed in the centrifuge tube 22 is moved to the vicinity of the disposal box 77, and then, the pipette 23 is discarded into the disposal box 77. Thereby, while the pipette 23 is moved to the disposal box 77, the liquid adhering to the pipette 23 is prevented from falling to the floor 2b of the isolator 2.

After discarding the used pipette 23 in this way, the first robot 6 holds a new pipette 23 from the pipette holder 75, and mounts the new pipette 23 to the third liquid supply/discharge means 71C.

The inspection means 11 is arranged in the movable range of the second robot 7. As shown in FIG. 12, the inspection means 11 is configured by imaging means 11a and illumination means 11b respectively provided at upper and lower portions of a vertically narrow observation space 11S protruding outwardly from the back surface side of the isolator 2.

The observation space 11S communicates with the work chamber 2a of the isolator 2, and each of the upper and lower surfaces of the observation space 11S is formed of a light-transmitting member, such as glass. The observation plate 25 held at the second robot 7 is inserted into the observation space 11S.

The imaging means 11a is arranged above the observation space 11S, and the illumination means 1ib is arranged below the observation space 11S. The light of the illumination means 1ib passes through the light-transmitting member and passes through the plate 25a of the observation plate 25, so that the imaging means 11a captures an enlarged image of the cells on the plate 25a.

Then, the control means 5 performs image processing of the image imaged by the imaging means 11a, and for example, counts the number of surviving cells and the number of dead cells in the observation range, to calculate the survival rate of the cells from the count values.

It should be noted that, by inserting, into the observation space 11S, the dish 21 mounted to the attachment 33, the control means 5 can obtain, by image processing, the cell occupancy in the mixture of the cells and the cultures which are housed in the dish 21.

Then, in the below-described passage culture work in the present embodiment, the culture medium, which is sucked from the culture medium container 29 by the first liquid supply/discharge means 71A constituting the culture medium supply means, is supplied to a new empty dish 21 as a second culture vessel held by the robot in the liquid supply means 10.

On the other hand, the third liquid supply/discharge means 71C, configuring the dispensing means, sucks the suspension of the cells and the culture medium from the centrifuge tube 22 as the first culture vessel. The suspension is transported by the robot and is dispensed to the dishes 21 as a plurality of the second culture vessels, so that the cells are dispensed to the new dishes 21.

In this case, in the present embodiment, the amount of the culture medium, which is newly required for the passage culture work at this time, is obtained on the basis of the results of the inspection by the inspection means 11, and the number of new dishes 21 to be dispensed is determined on the basis of the amount of the culture medium. The determining means for performing the determination is provided in the control means 5.

When the number of surviving cells is counted by the inspection means 11, the determining means determines whether or not the survival rate of the cells exceeds a predetermined threshold value. When the survival rate does not exceed the threshold value, a standard amount is selected as the amount of the culture medium to be used, and the passage culture work is performed in the standard passage mode in which the cells are passaged to the prescribed number of dishes 21 which is associated with the standard amount.

On the other hand, when the number of surviving cells exceeds the threshold value in the inspection result, many cells are alive, and hence, a larger amount of culture medium is required than when the passage culture work is performed in the standard passage mode.

For this reason, the determining means selects a larger amount of culture medium than the normal amount of culture medium. Thereby, the passage culture work is performed in the excellent passage mode in which the cells are passaged to a larger number of dishes 21 than in the standard passage mode.

For example, in the case where, in the standard passage mode, the cells housed in one centrifuge tube 22 are passaged to 10 new dishes 21, the cells are passaged to 15 new dishes 21 in the excellent passage mode.

It should be noted that the inspection of cells is performed by extracting a part of the cultured cells, and hence, the required amount of culture medium is calculated by multiplying the obtained number of surviving cells by a predetermined coefficient. Further, the calculated amount of culture medium to be dispensed is divided by the amount of culture medium housed in each of the dishes 21, and thereby, the number of dishes 21 is determined.

Further, the inspection means 11 and the determining means not only determine, in the passage culture work, the number of dishes 21 for the cultivation, but are also used for determining whether or not the passage operation is performed.

For example, a predetermined interval, for example, every morning at a fixed time, the second robot 7 takes out the dishes 21 from the incubator 4, and moves each of the dishes 21 with cells to the inspection means 11.

Then, the imaging means 11a of the inspection means 11 images the cells in the dish 21 to measure the occupation ratio of the cells in the image. Then, when, on the basis of the occupation rate of the cells, the control means 5 determines that the cells are sufficiently cultured, the control means 5 determines to perform the passage operation.

When the cells are observed by the observing means 11, trypan blue housed in the reagent container 32 is added to the cells mounted on the observation plate 25, and thereby, the number of surviving cells can be easily measured by the imaging means 11a.

For this reason, a reagent supply means 101 for supplying the trypan blue to the observation plate 25, and a nozzle exchange means 102 for exchanging the micropipette nozzle 35 of the micropipette 34 used for supplying the cells and the trypan blue to the observation plate 25 are provided in the work chamber 2a, and these types of work are automatically performed.

As shown in FIG. 13, the reagent supply means 101 is provided at the casing 45a housing the camera 45 and is provided in the movable range of the first and second robots 6 and 7.

A holding means 103 for holding the micropipette 34 is fixed to the casing 45a, and the centrifuge tube 22 for discarding the micropipette nozzle 35 is arranged below the held micropipette 34. Further, a reagent container holder 104 for holding the reagent container 32 is provided in the vicinity of the casing 45a.

On the upper surface of the holding means 103, the holding member 36 attached to the micropipette 34 is mounted, and also, positioning pins (not shown) fitted to the two positioning holes 36b provided in the holding member 36 are provided.

When the eject button 34c of the micropipette 34 is operated, the centrifuge tube 22 for discarding the micropipette nozzle 35 collects the dropped micropipette nozzle 35, and then, the micropipette nozzle 35 is discarded in the disposal box 77 together with the centrifuge tube 22.

The nozzle exchange means 102 is provided at a position adjacent to the rotary stocker 8 and is provided in the movable range of the first robot 6.

As shown in FIG. 14, the nozzle exchange means 102 is configured by holding means 103A having the same structure as the holding means 103 of the reagent supply means 101, and mounting means 105 by which the micropipette nozzle 35 provided below the holding means 103A is mounted to the distal end tube 34a of the micropipette 34.

The mounting means 105 is configured by a holding member 105a provided with a through hole for holding the micropipette nozzle 35, and elevating means 105b, such as an air cylinder, for raising and lowering the holding member 105a.

Further, in the present embodiment, the micropipette 34 is used as follows.

First, the first robot 6 holds the micropipette nozzle 35 from the specimen container supporting table 55 of the rotary stocker 8, and moves the micropipette nozzle 35 to the nozzle exchange means 102 so that the micropipette nozzle 35 is held by the holding member 105a of the mounting means 105.

Subsequently, the first robot 6 holds the micropipette 34 from the specimen container supporting table 55 so that the micropipette 34 is held by the holding means 103A of the nozzle exchange means 102.

At this time, the holding member 105a of the mounting means 105 is located at a lowered position by the elevating means 105b, and then, from this state, the holding member 105a is raised by the elevating means 105b so that the micropipette nozzle 35 is firmly mounted to the distal end tube 34a.

At this time, the first robot 6 presses the micropipette 34 from above so that the micropipette 34 does not come off from the holding means 103.

When the micropipette nozzle 35 is mounted to the micropipette 34 in this way, the first robot 6 moves the micropipette 34 to the reagent supply means 101.

Subsequently, the second robot 7 moves the centrifuge tube 22 housing the suspension containing the cells to a position below the micropipette 34 in the reagent supply means 101. Then, the first robot 6 operates the suction button 34b of the micropipette 34 so that the micropipette 34 sucks a small amount of the suspension.

Subsequently, the second robot 7 positions the observation plate 25 at a position below the micropipette 34, and then, the first robot 6 again operates the suction button 34b so that a predetermined amount of the suspension is discharged to the observation plate 25.

On the handing-over table 42, the second robot 7 mounts the observation plate 25 with the cells mounted thereon, and then, the first robot 6 operates the eject button 34c of the micropipette 34 so that the mounted micropipette nozzle 35 drops in the centrifuge tube 22.

Subsequently, the first robot 6 moves the micropipette 34 to the nozzle exchange means 102. Then, the first robot 6 attaches a new micropipette nozzle 35 to the micropipette 34, and again moves, to the reagent supply means 101, the micropipette 34 with the new micropipette nozzle 35 attached thereto.

The second robot 7 holds the reagent container 32 from the reagent container holder 104 and moves the reagent container 32 to the reagent supply means 101. The first robot 6 operates the micropipette 34 so that a predetermined amount of the reagent is sucked by the micropipette 34.

Next, the second robot 7 moves the observation plate 25 to a position below the micropipette 34, and the first robot 6 operates the micropipette 34 so that the reagent of the micropipette 34 is supplied to the cells on the observation plate 25.

Then, the second robot 7 moves the observation plate 25 to the observing means 11 so that the cells are observed.

On the other hand, the first robot 6 operates the micropipette 34 so that the used micropipette nozzles 35 is collected in the centrifuge tube 22, and then, the first robot 6 moves the micropipette 34 to the nozzle exchange means 102.

The space in the incubator 4 is maintained at the optimal temperature and humidity for the cell culture, and the isolator 2 and the incubator 4 are connected to each other by connection means 111. In this way, the automatic culturing device 1 of the present embodiment is provided with the incubator 4, and is configured as a culture device for culturing a culture object.

Further, the incubator 4 is made movable by means of a carriage 4a shown in FIG. 2, and it is possible to cultivate cells at a position away from the isolator 2.

Further, a rack (not shown) which houses a prescribed number of dishes 2, and carrying means 4b, which takes out a predetermined dish 21 from the rack and hands over the dish 21 to the carrying-in-and-out means 12 in the isolator 2, are provided in the incubator 4.

The carrying means 4b is provided with a holding section 4c having the same shape as that of the holding section 33b of the attachment 33, and holds the dish 21 at a required position of the rack by raising and lowering the holding section 4c.

As shown in FIG. 1, first and second communication ports 2dA and 2dB are respectively formed at the positions at which the two incubators 4 are connected to the side surface of the isolator 2. Each of the first and second communication ports 2dA and 2dB is opened and closed by an isolator side shutter 112 as communication port opening/closing member.

On the other hand, a carrying-in-and-out port 4d is formed in the side surface of the incubator 4. The carrying-in-and-out port 4d is opened and closed by an incubator side shutter 113 as a carrying-in-and-out opening/closing member.

Figure 15:
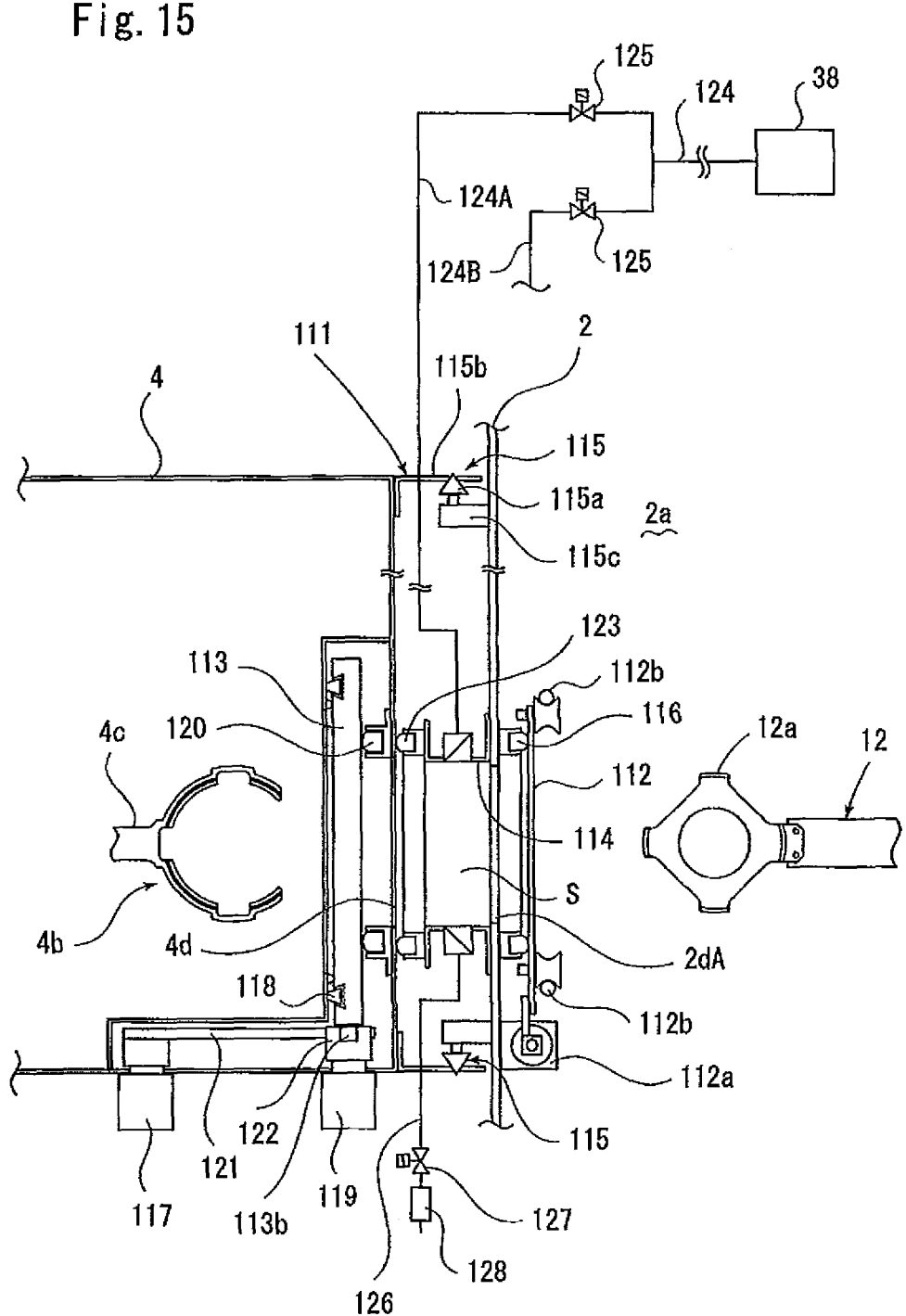
FIG. 15 is a plan view showing a connection means.

In the following, the connection means 111 connected to the first communication port 2dA will be described with reference to FIG. 15. The connection means 111 is provided with: a cylindrical connecting member 114 which surrounds the periphery of the communication port 2dA of the isolator 2 and the carrying-in-and-out port 4d of the incubator 4, and which is provided to maintain an airtight state on the side surface of the isolator 2, and on the side surface of the incubator 4; and a connection mechanism 115 which maintains the connection state between the isolator 2 and the incubator 4.

An annular hollow sealing member 116 is provided at the communication port 2dA of the isolator 2. The isolator side shutter 112 is provided so that it can be raised and lowered by an air cylinder 112a as drive means and by being guided by a guide rail 112b.

When the isolator side shutter 112 is located at the height position of the communication port 2d, air is supplied into the hollow sealing member 116, and thereby, the hollow sealing member 116 is expanded to be in close contact with the isolator side shutter 112 and is sealed.

By the driving force of an opening and closing motor 117 as drive means, the incubator side shutter 113 is raised and lowered under the guidance of a guide rail 118, to open and close the carrying-in-and-out port 4d of the incubator 4, and is maintained in the raised state by a lock motor 119.

When the incubator side shutter 113 is located at the height position of the carrying-in-and-out port 4d, air is supplied into an annular hollow sealing member 120 provided at the carrying-in-and-out port 4d, to inflate the hollow sealing member 120. Thereby, the hollow sealing member 120 is brought into close contact with the incubator side shutter 113 and is sealed.

The rotating shaft of the opening and closing motor 117 passes through the side wall of the incubator 4, and an arm 121 provided with a substantially U-shaped first concave section 121a is provided at the distal end of the rotating shaft.

The first concave section 121a is engaged with a first protrusion 113a provided at a side lower portion of the incubator side shutter 113. The arm 121 is swung up and down by the opening and closing motor 117 between the closed state shown in FIG. 16(a) and the opened state shown in FIG. 16(b), to press the first protrusion 113a in conjunction with the first concave section 121a, and thereby, the incubator side shutter 113 moves up and down.

The rotating shaft of the lock motor 119 also passes through the side wall of the incubator 4, and a substantially U-shaped second concave section 122a is formed at a rotating body 122 which is rotated by the rotating shaft. On the other hand, a second protrusion 113b engaging with the second concave section 122a is formed at a side portion of the incubator side shutter 113.

Figure 16:
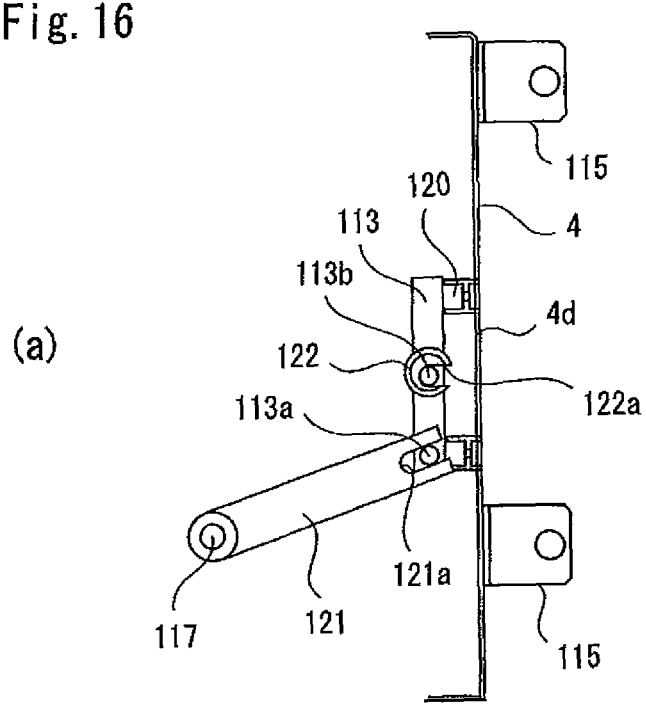
FIG. 16 is a side view of a shutter of an incubator.
Figure 16:
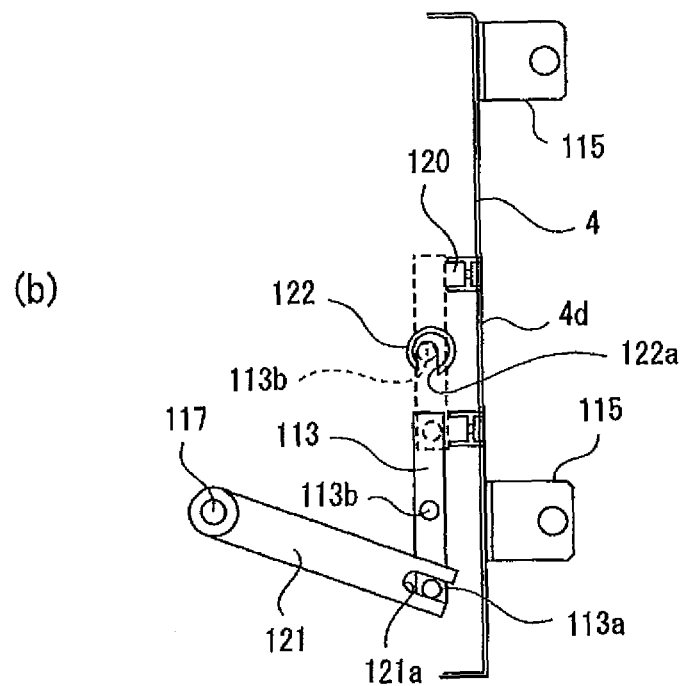

Further, in the rising state shown in FIG. 16(a), the second concave section 122a is directed in the lateral direction by the lock motor 119, and thereby, the vertical movement of the second protrusion 113b is prevented, so that the closed state of the incubator side shutter 113 is maintained.

For the opened state, the second concave section 122a is directed in the downward direction by the lock motor 119, and thereby, the downward movement of the second protrusion 113b is allowed, so that the incubator side shutter 113 can be opened.

In this way, since for each of the communication port 2d of the isolator 2, and the carrying-in-and-out port 4d of the incubator 4, the shutter, which is opened and closed by the drive means, is adopted as an opening and closing member, the opening/closing can be automatically operated, thereby eliminating the possibility of interference of the shutter with the movement of the second robot 7 and the carrying-in-and-out means 12 in shutter opening.

The connecting member 114 is fixed to the side surface of the isolator 2 and is a cylindrical member provided to surround each of the first and second communication ports 2dA and 2dB of the isolator 2, and an annular sealing member 123 is provided at the distal end of the connecting member 114, to surround and seal the outer wall side periphery of the carrying-in-and-out port 4d of the incubator 4.

Thereby, the decontamination space S, which is isolated from the outside atmosphere, can be formed between the isolators 2 and the incubators 4 which are connected to each other by the connecting member 114.

The connection mechanism 115 is configured by: four engaging pins 115a which are provided on the side surface of the isolator 2; four engaging hooks 115b which are provided on the side surface of the incubator 4 and respectively engage with the engaging pins 115a; and an air cylinder 115c which makes the engaging pins 115a advance and retreat.

The engaging pin 115a is protruded so that all the engaging pins 115a engage with the engaging hooks 115b, respectively. Thereby, the incubator 4 is connected and held to the isolator 2, so that the sealed decontamination space S is formed inside the connecting member 114.

Further, the decontamination gas is supplied, from the decontamination gas supply means 38 via a supply passage 124, to the connecting member 114 of each of the connection means 111 corresponding to each of the first and second communication ports 2dA and 2dB.

The supply passage 124 is branched to a passage 124A connected to the connecting member 114 provided at the first communication port 2dA, and a passage 124B connected to the connecting member 114 provided at the second communication port 2dB, and an opening/closing valve 125 controlled by the control means 5 is provided at each of the passage 124A and the passage 124B. Thereby, the switching means for supplying the decontamination gas to one of the connection means 111 is configured.

In this configuration, when the decontamination gas is supplied to one of the connecting members 114 via the supply passage 124, the decontamination gas is fully filled in the decontamination space S formed by the connecting member 114, so that the surfaces of the isolator side shutter 112 and the surface of the incubator side shutter 113, which surfaces are exposed to the outside atmosphere, can be decontaminated.

When the decontamination gas is supplied to the decontamination space S and when a predetermined time elapses, an opening/closing valve 127 of a discharge passage 126 provided at each of the connecting member 114 is opened, and thereby, the decontamination gas in the decontamination space S is detoxified by a catalyst 128 to be discharged. Thereafter, during a predetermined time, aeration is performed by flowing sterile air.

Then, the decontamination by the decontamination gas is performed when the incubator 4 is connected and disconnected.

Here, in the present embodiment, the narrow decontamination space S, which surrounds each of the first and second communication ports 2dA and 2dB of the isolator 2, and each of the carrying-in-and-out ports 4d of the incubator 4, is formed by the connecting member 114, and the narrow decontamination space S is decontaminated by the decontamination gas. Therefore, the decontamination space S can be decontaminated in a relatively shorter time than when the space with the large volume is decontaminated.

The carrying-in-and-out means 12 performing the carrying in and out of the dish 21 between the isolator 2 and the incubators 4 are provided in the vicinities of the two communication ports 2dA and 2dB, respectively.

The carrying-in-and-out means 12 is configured by a dish mounting section 12a for mounting the dish 21, and a moving means 12b for horizontally moving the dish mounting section 12a.

The dish mounting section 12a has the same shape as that of the dish mounting section 60 of the dish mounting table 53 in the rotary stocker 8, and is reciprocated, by the moving means 12b, between within the working range of the second robot 7 and the insides of the incubator 4.

When the dish mounting section 60 is located at a position on the side of the second robot 7 by the moving means 12b, the handing over the dish 21 is performed via the attachment 33 held by the second robot 7. At this position, the dish 21 is carried in and out of the incubator 4 by the second robot 7.

Further, when the dish mounting section 60 is located in the incubator 4, the handing over the dish 21 is performed between the dish mounting section 60 and the carrying means 4b of the incubator 4.

In the following, the operation of the automatic culturing device 1 having the above-described configuration will be described.

Before the cultivating operation using the first and second robots 6 and 7 is performed, instruments and containers are carried in the isolator 2 from the pass box 3, and then, a worker manually performs the preliminary work for arranging the instruments and the containers at predetermined positions.

First, the worker opens the external opening and closing door 3a of the pass box 3, and hangs the packaging bag B, housing the instruments and the containers, on the hook 3b in the pass box 3, so that the outer surface of the packaging bag B is decontaminated by the decontamination gas of the decontamination gas supply means 38.

The worker wears the carrying-in-and-out gloves 40a provided in the isolator 2 and the pass box 3, and then carries the packaging bag B in the pass box 3 into the work chamber 2a of the isolator 2.

At this time, the worker switches the switching means of the rotary stocker 8 to the non-transmission state, and then manually rotates each of the tables 52 to 55 so that the dishes 21 and the centrifuge tubes 22 are respectively housed in the tables 52 to 55, and the pipettes 23 are mounted in the pipette holder 75.

Further, the worker mounts the aspirator nozzle 24 to the moving table 41, and further discards, to the disposal box 77, the packaging bag B, from which the instruments and the containers are taken out.

Next, the worker carries the specimen containers 28 and the liquids into the pass box 3 through the external opening and closing door 3a of the pass box 3, and further, wears the carrying-in-and-out glove 40a and wipes, with an antiseptic solution, the specimen containers 28 and the liquid containers 29 to 32 housing the liquids.

Subsequently, the worker opens the opening and closing door 39 and carries the liquids into the isolator 2. Specifically, the worker puts the specimen containers 28 and the reagent containers 32 in the rotary stocker 8, and then, respectively mounts the culture medium container 29, the PBS container 30, and the trypsin container 31 to the moving table 41.

At this time, the worker exchanges the screw type caps respectively attached to the centrifuge tube 22, the specimen container 28, and the liquid containers 29 to 32 for the cover caps 26, each of which does not need a rotating operation.

When the worker manually moves the moving table 41 to the front of the liquid supply means 10, the worker further wears the arrangement glove 40b, and attaches the aspirator nozzle 24 on the moving table 41 to the aspirator 73, and also, arranges the liquid containers 29 to 31 at predetermined positions.

It should be noted that the attachment 33 and the micropipette 34 are mounted beforehand to the isolator 2, but these may be housed in the packaging bag B to be carried in from the outside each time the cultivating operation is performed In this way, when the carrying-in work and arrangement work of the instruments, the containers, and the liquids are performed by a robot, the work becomes complicated, and hence, the work is performed by the worker more promptly than by the robot.

When the these kinds of preparation work are completed, the automatic cultivating operation can be performed by the control means 5 using the first and second robots 6 and 7, the liquid supply means 10, and the like. Before each of the cultivating operations is performed, the following work is performed by control of the control means 5.

First, by controlling the first robot 6, the control means 5 respectively attaches the pipettes 23 mounted in the pipette holder 75 to the first to third liquid supply/discharge means 71A to 71C of the liquid supply means 10.

At the same time, the control means 5 performs the operation of returning the switching means 58 of the rotary stocker 8 to the transmission state. Specifically, the operation is performed in such a manner that, when the switching means 58 is set in the non-transmission state in the preparation work, the pulley 62 is rotated by the drive means 57, and thereby, the pulley 62 is rotated relatively to the connecting member 61, and that, when the pulley 62 is further rotated, the ball 63 is fitted to the concave section 62a of the pulley, and thereby, the connecting member 61 is moved upwards so that the switching means 58 is set to the transmission state.

When the switching means 58 is set to the transmission state in this way, the control means 5 further rotates the rotating shaft 51 with the drive means 57, so that the detection piece 59a provided at the rotating shaft 51 is recognized by the rotation position sensor 59, and the containers and the instruments respectively mounted in the tables 52 to 55 by the worker are recognized by the instrument sensor 57.

Thereby, the control means 5 can recognize the rotational position of each of the tables 52 to 55, and recognize the position and the presence or absence of each of the instruments and the containers which are respectively mounted in the tables 52 to 55.

As the following cultivating operation, there are described the sowing work for housing the cells in the culture vessel together with the culture medium, the culture medium exchange work for exchanging the old culture medium, the passage culture work for distributing the cells of one culture vessel to a plurality of new culture vessels, and the collection work for collecting the cells whose cultivation is ended.

It should be noted that, in the cultivating operation, the operation of each of the first and second robots 6 and 7, the liquid supply means 10, and the like, is operated according to the operation registered beforehand in the control means 5, but the following operation is only an example, and needless to say, the cultivating operation may also be performed with a different sequence of operation, and work other than the work described above may also be performed.

Figure 17:
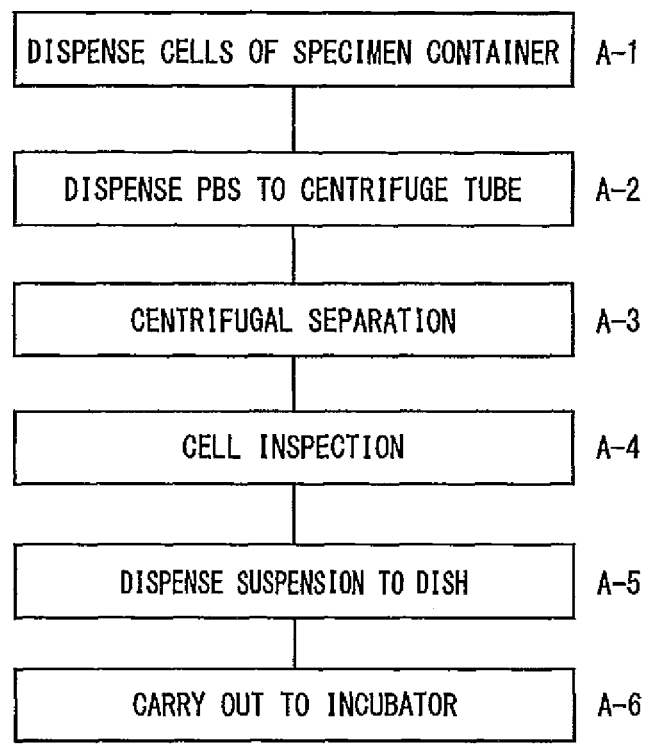
FIG. 17 is a flow diagram for explaining sowing work.

FIG. 17 shows a flow of the sowing work in which the dish 21 and the centrifuge tube 22 as the containers, the pipette 23 and the aspirator nozzle 24 as the instruments, and the culture medium container 29, the PBS container 30, and the reagent container 32 as liquids, are respectively carried from the pass box 3 into the isolator 2. Further, apart from these, the specimen container 28 containing cells is carried from the pass box 3 into the isolator 2.

First, the work of dispensing cells of the specimen container 28 to a plurality of the centrifuge tubes 22 is performed (A-1).

The first robot 6 takes out the specimen container 28 from the rotary stocker 8, and moves the specimen container 28 to the third liquid supply/discharge means 71C of the liquid supply means 10 so that the pipette 23 sucks the liquid of the specimen container 28, which liquid contains the cells.

The first robot 6 discards the empty specimen container 28 to the disposal box 77, and subsequently takes out the empty centrifuge tube 22 from the rotary stocker 8 to move the empty centrifuge tube 22 to the third liquid supply/discharge means 71C, so that a predetermined amount of the cells are dispensed from the pipette 23 to the centrifuge tube 22.

Then, the first robot 6 operates so that the centrifuge tube 22, to which the cells are dispensed, is held by the centrifuge tube holder 43.

Next, the work of dispensing the PBS into the centrifuge tube 22 is performed (A-2).

The second liquid supply/discharge means 71B and the second container holding means 72B of the liquid supply means 10 are operated so that a predetermined amount of PBS is sucked into the pipette 23.

Subsequently, the first robot 6 takes out the centrifuge tube 22 supported by the centrifuge tube holder 43 and moves the centrifuge tube 22 to the second liquid supply/ discharge means 71B, so that a predetermined amount of PBS is discharged into the centrifuge tube 22 from the pipette 23.

Then, the first robot 6 operates so that the centrifuge tube 22, to which the PBS is dispensed, is again supported by the centrifuge tube holder 43.

Next, the work of centrifuging the dispensed cells of the PBS is performed (A-3).

The second robot 7 takes out the centrifuge tube 22 supported by the centrifuge tube holder 43 and houses the centrifuge tube 22 in the centrifugal separation means 9. At this time, a counter weight is created with a new centrifuge tube 22 by the second robot 7 and the liquid supply means 10.

Subsequently, the centrifugal separation means 9 is operated, and thereby, the liquid in the centrifuge tube 22 is separated into the lower liquid containing the cells, and a supernatant.

When the centrifugal separation is completed, then the second robot 7 takes out the centrifuge tube 22 from the centrifugal separation means 9 and moves the centrifuge tube 22 to the aspirator 73, which sucks and removes the supernatant in the centrifuge tube 22.

Then, the second robot 7 operates so that the centrifuge tube 22, from which the supernatant is removed, is supported by the centrifuge tube holder 43.

Next, the inspection of the cells in the centrifuge tube 22 is conducted (A-4).

The first liquid supply/discharge means 71A and the first container holding means 72A of the liquid supply means 10 are operated so that a predetermined amount of culture medium is sucked into the pipette 23.

Subsequently, the first robot 6 takes out the centrifuge tube 22 of the centrifuge tube holder 43 and moves the centrifuge tube 22 to the first liquid supply/discharge means 71A in which a predetermined amount of culture medium is discharged from the pipette 23 into the centrifuge tube 22.

Then, the first robot 6 operates so that the centrifuge tube 22, to which the culture medium is dispensed, is supported by the centrifuge tube holder 43.

Thereafter, the observation plate 25 is held by the first and second robots 6 and 7, and in the inspection means 11, a part of the cells in the centrifuge tube 22 is inspected on the basis of the procedure described above.

The centrifuge tube 22, from which an inspected part of the cells is collected, is again supported by the centrifuge tube holder 43.

Next, the work of creating a suspension by the culture medium and the cells and carrying the suspension to the dish 21 is performed (A-5).

The first robot 6 houses, in the pipette holder 75, the pipette 23 of the third liquid supply/discharge means 71C, which pipette is used at the time when the liquid containing the cells is sucked from the specimen container 28 in the work B-1. Then, the first robot 6 exchanges the used pipette 23 for the new pipette 23, and discards the used pipette 23 to the disposal box 77.

The second robot 7 takes out the centrifuge tube 22 of the centrifuge tube holder 43 and moves the centrifuge tube 22 to the third liquid supply/discharge means 71C, in which the suspension is created by sucking and discharging the liquid in the centrifuge tube 22 to and from the pipette 23, so that the suspension is sucked into the pipette 23.

The second robot 7 hands over the empty centrifuge tube 22 to the first robot 6 via the centrifuge tube holder 43, and the first robot 6 discards the empty centrifuge tube 22 to the disposal box 77.

Next, the first robot 6 takes out the new dish 21 from the rotary stocker 8 by using the attachment 33, and moves the new dish 21 to the third liquid supply/discharge means 71C, in which the suspension is discharged to the dish 21 from the pipette 23.

Then, the first robot 6 mounts the dish 21 to which the suspension is dispensed, to the handing-over table 42 together with the attachment 33.

Finally, the work of carrying the dish 21 to which the suspension is dispensed, to the incubator 4 is performed (A-6).

First, the second robot 7 holds the dish 21 mounted to the handing-over table 42, together with the attachment 33, and mounts the dish 21 to the carrying-in-and-out means 12.

When the isolator side shutter 112 and the incubator side shutter 113 are opened, the carrying-in-and-out means 12 moves the dish 21 into the incubator 4 and hands over the dish 21 to the carrying means 4b of the incubator 4.

Here, in the work for dispensing the suspension in A-5, the suspension sucked into the third liquid supply/discharge means 71C is dispensed to a plurality of the dishes 21. For this reason, the work A-5 and the work A-6 are repeated, and thereby, a predetermined number of the dishes 21 are housed in the incubator 4.

Figure 18:
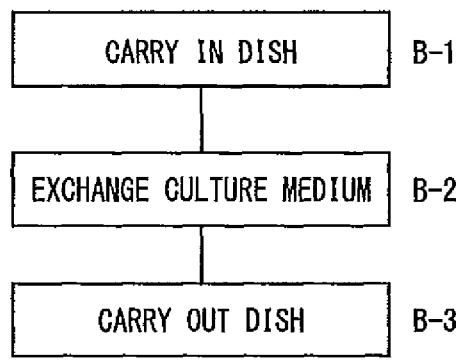
FIG. 18 is a flow diagram for explaining culture medium exchange work.

FIG. 18 shows a flow of culture medium exchange work, in which the dish 21 housing the cultured cells is housed in the incubator 4 connected to the isolator 2, and in which, in the isolator 2, the pipette 23 and the aspirator nozzle 24 as instruments, and the culture medium container 29 as liquids are mounted beforehand.

First, the work of taking out the dish 21 in the incubator 4 is performed (B-1).

The incubator side shutter 113 and the isolator side shutter 112 are opened, and the carrying-in-and-out means 12 moves the dish mounting section 12a to the inside of the incubator 4.

When the carrying-in-and-out means 12 receives the dish 21 from the carrying means 4b in the incubator 4, the carrying-in-and-out means 12 moves the dish 21 into the isolator 2, and the second robot 7 receives the dish 21.

Next, the work to replace the old culture medium in the dish 21 with a new culture medium is performed (B-2).

The second robot 7, holding the dish 21, moves the dish 21 to the aspirator 73, so that the old culture medium in the dish 21 is sucked and removed by the aspirator 73.

On the other hand, the first liquid supply/discharge means 71A and the first container holding means 72A in the liquid supply means 10 are operated, and a predetermined amount of the culture medium is sucked by the pipette 23.

Thereafter, the second robot 7 moves the dish 21, from which the used culture medium is removed, to the first liquid supply/discharge means 71A, and then, a predetermined amount of the culture medium is discharged to the dish 21 from the pipette 23, so that the exchange of the culture medium is completed.

Finally, the work of carrying the dish 21 to the incubator 4 is performed (B-3).

The second robot 7 hands over the dish 21 to the dish mounting section 12a of the carrying-in-and-out means 12 located at the handing-over position in the movable range of the second robot 7. The carrying-in-and-out means 12 moves the dish 21 to the inside of the incubator 4, and in the incubator 4, the carrying means 4b mounts the dish 21 in a predetermined rack.

Then, the control means 5 repeats each of the work B-1 to the work B-3 for all the dishes 21 in the incubator 4, so that the culture-medium exchange of all the dishes 21 is performed.

Figure 19:
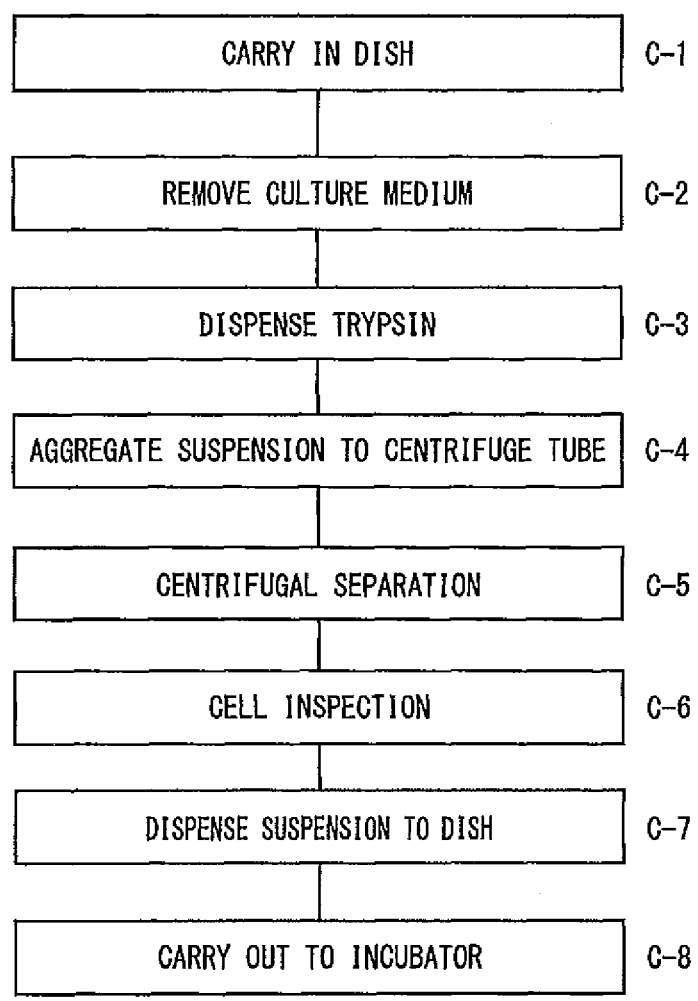
FIG. 19 is a flow diagram for explaining passage culture work.

FIG. 19 shows a flow of passage culture work. In this case, the dish 21 housing the cells is housed in the incubator 4 connected to the isolator 2, and further, the dish 21 and the centrifuge tube 22 as the container, the pipette 23, the aspirator nozzle 24 as the instruments, and the culture medium container 29, the trypsin container 31, the reagent container 32 as the liquids are carried into the isolator 2.

First, the work of carrying out the dish 21 in the incubator 4 (C-1), and the work of removing the old culture medium from the dish 21 (C-2) are the same as the work B-1 and the work B-2 for culture medium replacement, and hence, the detailed description of the work (C-1) and the work (C-2) is omitted.

Further, the dish 21, from which the culture medium is removed, is mounted to the handing-over table 42 together with the attachment 33.

Next, the work of dispensing the trypsin to the dish 21 is performed (C-3).

The second robot 7 takes out the trypsin container 31 together with the container holder 76, and moves the trypsin container 31 to the second liquid supply/discharge means 71B, so that the Trypsin is sucked into the pipette 23. The PBS is not used in the passage culture work, and hence in the present work, the trypsin can be sucked by the second liquid supply/discharge means 71B.

Thereafter, the first robot 6 holds the dish 21 on the handing-over table 42 and moves the dish 21 to the second liquid supply/discharge means 71B, so that the second liquid supply/discharge means 71B discharges the trypsin of the pipette 23 to the dish 21.

Then, the first robot 6 houses the dish 21 to which the trypsin is dispensed, in the heated room 44 together with the attachment 33, so that the dish 21 is heated to a predetermined temperature in the heated room 44.

Next, the work of aggregating the suspension consisting of the cells and the trypsin to one centrifuge tube 22 is performed (C-4).

The second robot 7 takes out the dish 21 heated to the predetermined temperature in the heated room 44. At this time, the second robot 7 moves the dish 21 to the tapping means 46 of the heated room 44, so that, in the tapping means 46, the cells sticking to the bottom of the dish 21 are peeled off by giving vibration to the dish 21.

Subsequently, the second robot 7 moves the dish 21 to the third liquid supply/discharge means 71C, so that the cells and the trypsin in the dish 21 are repeatedly sucked and discharged into and from the pipette 23 to create the suspension, which is then sucked into the pipette 23.

Then, the second robot 7 hands over the empty dish 21 to the first robot 6, so that the empty dish 21 is discarded to the disposal box 77.

On the other hand, the first robot 6 holds the empty centrifuge tube 22 from the rotary stocker 8, and moves the empty centrifuge tube 22 to the third supply/discharge means 71C, so that the suspension is discharged to the centrifuge tube 22 from the pipette 23.

The second robot 7 repeats the above-described operation for the dishes 21 housed in the heated room 44, and thereby, the suspension housed in each of a plurality of the dishes 21 is aggregated in the centrifuge tube 22 held by the first robot 6.

Then, when a predetermined amount of the suspension is housed in the centrifuge tube 22, the first robot 6 makes the centrifuge tube holder 43 support the centrifuge tube 22.

Subsequently, the work of centrifuging the suspension in the centrifuge tube 22 (C-5), and the work of inspecting the cells (C-6), the work of creating the suspension with the culture medium and dispensing the suspension to the dish 21 (C-7), and the work of carrying the dish 21 to the incubator 4 (C-8) are performed.

These types of work are the same as those in A-3 to A-6 in the sowing work, but in the work of inspecting the cells in C-6, the number of the dishes 21, to which the suspension is distributed, is determined by the determining means provided in the control means 5.

Specifically, in the work of inspecting the cells in C-6, the number of surviving cells on the observation plate 25 is measured by the inspection means 11. Then, the newly required amount of the culture medium is obtained on the basis of the number of surviving cells, and then, on the basis of the obtained amount of the culture medium, it is determined whether the operation in C-7 is performed in the usual passage mode or the excellent passage mode.

When it is determined by the determining means that the dispensation work in C-7 is performed in the usual passage mode, the control means 5 controls the first and second robots 6 and 7 and the liquid supply means 10 so that the suspension containing the cells aggregated in the one centrifuge tube 22 as the first culture vessel is dispensed to, for example, the ten dishes 21 as the second culture vessels.

At this time, the control means 5 controls the first liquid supply/discharge means 71A and the first container holding means 72A so that the total amount of the culture medium to be dispensed to the ten dishes 21 is sucked into the pipette 23 of the first liquid supply/discharge means 71A.

On the other hand, when it is determined by the determining means that the dispensation work in C-7 is performed by the excellent passage mode, the control means 5 dispenses, for example, to the fifteen dishes 21, the suspension containing the cells and housed in the centrifuge tube 22.

At this time, the control means 5 controls the first liquid supply/discharge means 71A and the first container holding means 72A so that the total amount of the culture medium to be dispensed to the fifteen dishes 21 is sucked into the pipette 23 of the first liquid supply/discharge means 71A. It should be noted that, when the whole amount of the culture medium cannot be sucked at a time, it is also possible to perform suction and discharge separately a plural number of times, and also, it is possible to perform suction and discharge separately for each of the dishes 21. Therefore, the first and second robots 6 and 7 and the liquid supply means 10 may be controlled to repeat the same operation the same number of times as the number of the dishes 21.

It should be noted that the newly required amount of the culture medium can be obtained by multiplying the measured number of surviving cells by a predetermined coefficient, and hence, the number of the dishes 21, to each of which the culture medium is distributed, may also be obtained from the amount of the culture medium housed in the one dish 21, which amount corresponds to the obtained amount of the culture medium.

In this way, in the passage culture work, the cells are distributed to the dishes 21 more than the number of the dishes 21 taken out from the incubator 4. Therefore, when all the dishes 21 cannot be housed in one of the incubators 4 in the work for carrying the dishes 21 in the incubator 4 in C-8, the dishes 21 are housed in the other incubator 4.

At this time, in the case where all the dishes 21 cannot be housed in the two incubators 4 connected to the isolator 2 at the time of starting the cultivating operation, when the housing of the dishes 21 in the first incubator 4 as one of the two incubators 4 is completed, then, while the second incubator 4 is made to communicate with the work chambers 2a, the decontamination space S of the connection means 111 of the first incubator 4 is immediately decontaminated to detach the first incubator 4 from the connection means 111, and the third incubator 4 is connected to the connection means 111.

Then, while the second incubator 4 is made to communicate with the work chamber 2a, and in this state, the dishes 21 are carried in the second incubator 4, the decontamination of the decontamination space S of the connection means 111 of the third incubator 4 is performed, and thereby, the work chamber 2a is made to communicate with the third incubator 4, so that the dishes 21 can be carried in the third incubator 4.

At this time, it is only necessary to decontaminate the narrow decontamination space of the connection means 111 in the present embodiment described above. Therefore, the detachment of the first incubator 4, and the connection of the third incubator 4 can be performed quickly, and hence, the passage culture work can be efficiently performed.

Further, since the decontamination is performed at the time of detachment of the incubator 4, viruses, and the like, specific to the specimen are prevented from leaking to the outside from the inside of the work chamber 2a. Further, since the decontamination is performed at the time of connection of the incubator 4, external bacteria and microorganisms are prevented from being carried into the work chamber 2a.

Figure 20:
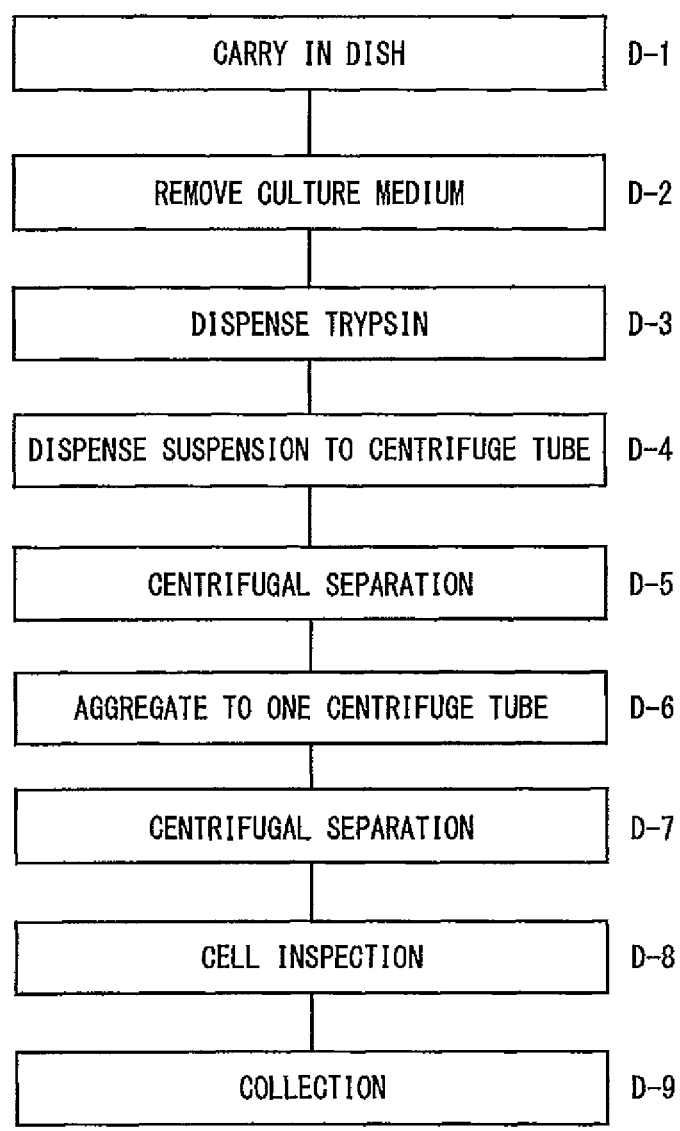
FIG. 20 is a flow diagram for explaining collection work.

FIG. 20 shows a flow of the collection work, in which the dish 21 housing the cells is housed in the incubator 4 connected to the isolator 2, and in which the dish 21 and the centrifuge tube 22 as the containers, and the pipette 23 and the aspirator nozzle 24 as the instruments are carried from the pass box 3, and also, the liquids, the culture medium container 29, the trypsin container 31, and the reagent container 32 are respectively carried from the pass box 3.

In the collection work, the work of carrying out the dish 21 from the incubator 4 (D-1), the work of removing the old culture medium from the dish 21 (D-2), the work of dispensing the trypsin to the dish 21 (D-3), the work of dispensing the suspension to the centrifuge tube 22 (D-4), and the work of centrifuging the suspension of the centrifuge tube 22 (D-5) are performed. These types of work are the same as those in C-1 to C-7 in the passage culture work, and hence, the detailed description of these types of work is omitted.

Further, as a result of the centrifugal separation work in D-5 described above, a plurality of the centrifuge tubes 22, each housing the cells, from which the supernatant is removed, are obtained and supported by the centrifuge tube holder 43.

Subsequently, the work of aggregating the centrifuged cells to the one centrifuge tube 22 is performed (D-6).

In the first liquid supply/discharge means 71A, and the first container holding means 72A, the culture medium is sucked to the pipette 23. The second robot 7 takes out the centrifuge tube 22 of the centrifuge tube holder 43, and moves the centrifuge tube 22 to the first liquid supply/discharge means 71A, so that the culture medium is discharged to the centrifuge tube 22 from the pipette 23.

Further, the second robot 7 makes the centrifuge tube holder 43 support the centrifuge tube 22 to which the culture medium is dispensed.

On the other hand, the first robot 6 exchanges the pipette 23 used for removing the culture medium in D-2 by the third liquid supply/discharge means 71C, for the new pipette 23 housed in the pipette holder 75 beforehand, and discards the used pipette 23 to the disposal box 77.

Subsequently, from the centrifuge tube holder 43, the first robot 6 takes out the centrifuge tube 22 to which the culture medium is dispensed. Then, the first robot 6 moves the centrifuge tube 22 to the third liquid supply/discharge means 71C, so that the culture medium and the cells in the centrifuge tube 22 are repeatedly sucked and discharged to and from the pipette 23 to create a suspension, and the suspension is sucked to the pipette 23.

Then, the first robot 6 discards the used centrifuge tube 22 to the disposal box 77.

Subsequently, the first robot 6 takes out the new centrifuge tube 22 from the rotary stocker 8, and moves the new centrifuge tube 22 to the third liquid supply/discharge means 71C, so that the suspension is discharged to the new centrifuge tube 22 from the pipette 23.

The control means 5 creates the suspension for all the centrifuge tubes 22 supported by the centrifuge tube holder 43 in the work D-5, and aggregates the suspension to one new centrifuge tube 22 held by the first robot 6.

At this time, in the case where all the cells housed in the incubator 4 cannot be processed in the centrifugal separation means 9 in one cycle of the work D-1 to the work D-5, the second cycle of the work D-1 to the work D-5 is repeatedly performed while the work D-6 is performed, and the suspension obtained by the second cycles of the work D-1 to the work D-5 is aggregated to one centrifuge tube 22.

Further, the first robot 6 makes the centrifuge tube holder 43 support the centrifuge tube 22 to which the suspension is dispensed.

Next, the work of centrifugally separating the cells aggregated in the one centrifuge tube 22 is again performed (D-7).

The second robot 7 takes out the centrifuge tube 22 housing the suspension from the centrifuge tube holder 43, and houses the centrifuge tube 22 in the centrifugal separation means 9, so that the suspension in the centrifuge tube 22 is centrifuged by the centrifugal separation means 9.

When the centrifugal separation is completed, the second robot 7 takes out the centrifuge tube 22, and moves the centrifuge tube 22 to the aspirator 73, so that the supernatant is removed from the centrifuge tube 22 by the aspirator 73.

Next, the work of inspecting the cells in the centrifuge tube 22, from which the supernatant is removed, is performed (D-8).

The inspection work in D-8 is the same as the inspection work in C-6 of the passage culture work, and hence, the detailed description of the inspection work is omitted.

Finally, the work of collecting the cells is performed (D-9).

When the inspection is completed, the first robot 6 houses the centrifuge tube 22 in the rotary stocker 8, and the control means 5 stops the operation of the first and second robots 6 and 7, and the like.

Thereafter, the worker wears the carrying-in-and-out glove 40a, and carries out the centrifuge tube 22 housing the cells via the pass box 3.

As shown in the present embodiment, the automatic culturing device 1 of the present embodiment is provided with the robots in the work chamber 2a of the isolator 2. The robots are provided so that the first robot 6 is provided for the rotary stocker 8, and the second robot 7 is provided for the incubator 4 and the centrifugal separation means 9.

Thereby, the containers housed in the rotary stocker 8 can be taken out by the first robot 6. Further, the operation of carrying the culture vessel into and out of the incubator 4, or the setting of the centrifuge tube to the centrifugal separation means 9 can be performed by the second robot 7, and hence, the cultivating operation can be efficiently performed by work sharing.

At this time, the handing-over table 42, the centrifuge tube holder 43, and the heated room 44, which are used as the temporary placement section, are provided for handing over the containers between the first robot 6 and the second robot 7, and the first robot 6 and the second robot 7 are provided for handing over the containers therebetween.

For this reason, for example, even when one of the robots is working, the other of the robots can mount the containers in the temporary placement section, to thereby perform another work.

Further, in the present embodiment, the rotary stocker 8 is arranged in the work chamber 2a of the isolator 2 and in the vicinity of the pass box 3, and also, the carrying-in-and-out glove 40a is provided so that work can be performed for the pass box 3 and the rotary stocker 8.

For this reason, when the containers are carried from the pass box 3 to the isolator 2 to be housed in the rotary stocker 8, this carrying-in operation can be performed by the worker wearing the carrying-in-and-out glove 40a, and hence, the operations, which are complicated at the time of using the robots, can be quickly performed.

REFERENCE SIGN LIST

1 Automatic culturing device
2 Isolator
2a Work chamber
3 Pass box
4 Incubator
5 Control means
6 First robot
7 Second robot
8 Rotary stocker
9 Centrifugal separation means
10 Liquid supply/discharge means
11 Inspection means
12 Carrying-in-and-out means
33 Attachment
34 Micropipette
40 Glove
40a Carrying-in-and-out glove
40b Arrangement glove
42 Handing-over table
43 Centrifuge tube holder
44 Heated room
52 Attachment mounting table
53 Dish mounting table
54 Centrifuge tube supporting table
55 Specimen container supporting table
57 Drive means
58 Switching means
60 Dish mounting section
71A-71C First to third liquid supply/discharge means
72A,72B First and second container holding means
73 Aspirator
77 Disposal box
111 Connection means
114 Connecting member

The invention claimed is:

1. An automatic culturing device comprising a work chamber maintained in a sterile state, a pass box connected to one side surface of the work chamber, and an incubator connected to the other side surface of the work chamber, the automatic culturing device including,
   in the work chamber, a rotary stocker which is arranged in the vicinity of the pass box and houses a culture vessel, a robot which holds and transports the culture vessel, and a pipette which supplies liquids, such as a culture medium and liquid medicine, to the culture vessel held by the robot, and the automatic culturing device being configured to perform a cultivating operation associated with the cultivation of a culture object by the robot,
   the automatic culturing device being characterized by including, as the robot, a first robot corresponding to the rotary stocker and a second robot corresponding to the incubator, the first and second robots respectively having movable ranges which partially overlap with each other, wherein
   the pipette and a handing-over table for handing over the culture vessel between the first and second robots are provided in the movable ranges of the first and second robots which overlap with each other,
   an attachment for supporting the culture vessel from the bottom is further provided and the attachment is housed in the rotary stocker,
   the first robot holds the attachment housed in the rotary stocker, causes the attachment to support and takes out the culture vessel housed in the rotary stocker, and mounts the attachment supporting the culture vessel on the housing-over table, and
   the second robot holds and transports the attachment mounted on the handing-over table and supporting the culture vessel.

2. The automatic culturing device according to claim 1, characterized in
   that a communication port is formed at a position at which the incubator is connected to the work chamber, and a dish mounting section at which the culture vessel is mounted and which is reciprocated between the second robot and inside of the incubator is provided and in the vicinity of the communication port, wherein
   the second robot transports the culture vessel housing the culture object and the culture medium between the hanging over table and the dish mounting section.

3. The automatic culturing device according to claim 2, characterized in that: a pass box for carrying the culture vessel into the work chamber from the outside is provided outside the work chamber and the rotary stocker is arranged in the vicinity of a communication port between the pass box and the work chamber.

4. The automatic culturing device according to claim 1, characterized in that: a pass box for carrying the culture vessel into the work chamber from the outside is provided outside the work chamber and the rotary stocker is arranged in the vicinity of a communication port between the pass box and the work chamber.

5. The automatic culturing device according to claim 1, wherein the liquids supplied by the pipette is at least one of a culture medium and medicine.

* * * * *